(12) United States Patent
Conkling et al.

(10) Patent No.: US 7,189,570 B2
(45) Date of Patent: Mar. 13, 2007

(54) PUTRESCINE-N-METHYLTRANSFERASE PROMOTER

(75) Inventors: Mark Conkling, Chapel Hill, NC (US); Yan Li, Durham, NC (US)

(73) Assignee: North Carolina State University, Raleigh, NC (US)

( * ) Notice: Subject to any disclaimer, the term of this patent is extended or adjusted under 35 U.S.C. 154(b) by 426 days.

(21) Appl. No.: 10/416,120

(22) PCT Filed: Nov. 7, 2001

(86) PCT No.: PCT/US01/47371

§ 371 (c)(1),
(2), (4) Date: Aug. 20, 2003

(87) PCT Pub. No.: WO02/38588

PCT Pub. Date: May 16, 2002

(65) Prior Publication Data

US 2004/0031074 A1 Feb. 12, 2004

Related U.S. Application Data

(60) Provisional application No. 60/246,448, filed on Nov. 7, 2000.

(51) Int. Cl.
C07H 21/04 (2006.01)
C12N 5/14 (2006.01)
C12N 15/82 (2006.01)
A01H 1/00 (2006.01)

(52) U.S. Cl. .................. 435/468; 536/24.1; 435/320.1; 435/419

(58) Field of Classification Search ...................... None
See application file for complete search history.

(56) References Cited

U.S. PATENT DOCUMENTS

| | | | |
|---|---|---|---|
| 4,693,976 A | 9/1987 | Schilperoort et al. | |
| 4,751,348 A | 6/1988 | Malmberg et al. ............. | 800/1 |
| 4,762,785 A | 8/1988 | Comai | |
| 4,885,248 A | 12/1989 | Ahlquist | |
| 4,940,838 A | 7/1990 | Schilperoort et al. | |
| 4,943,674 A | 7/1990 | Houck et al. | |
| 4,945,050 A | 7/1990 | Sanford et al. | |
| 4,954,442 A | 9/1990 | Gelvin et al. | |
| 4,962,028 A | 10/1990 | Bedbrook et al. | |
| 5,023,179 A * | 6/1991 | Lam et al. .................. | 800/287 |
| 5,034,322 A | 7/1991 | Rogers et al. | |
| 5,036,006 A | 7/1991 | Sanford et al. | |
| 5,097,025 A | 3/1992 | Benfey et al. | |
| 5,100,792 A | 3/1992 | Sanford et al. | |
| 5,107,065 A | 4/1992 | Shewmaker et al. | |
| 5,149,645 A | 9/1992 | Hoekema et al. | |
| 5,157,115 A | 10/1992 | Taniguchi | |
| 5,177,308 A | 1/1993 | Barton et al. | |
| 5,179,022 A | 1/1993 | Sanford et al. | |
| 5,190,931 A | 3/1993 | Inouye et al. | |
| 5,204,253 A | 4/1993 | Sanford et al. | |
| 5,208,149 A | 5/1993 | Inouye et al. | |
| 5,229,292 A | 7/1993 | Stock et al. | |
| 5,231,020 A | 7/1993 | Jorgensen et al. | |
| 5,254,800 A | 10/1993 | Bird et al. | |
| 5,260,205 A | 11/1993 | Nakatani et al. ............ | 435/193 |
| 5,272,065 A | 12/1993 | Inouye et al. | |
| 5,283,184 A | 2/1994 | Jorgensen et al. | |
| 5,352,605 A | 10/1994 | Fraley et al. | |
| 5,356,799 A | 10/1994 | Fabijanski et al. | |
| 5,365,015 A | 11/1994 | Grierson et al. | |
| 5,369,023 A | 11/1994 | Nakatani et al. ............ | 435/193 |
| 5,371,015 A | 12/1994 | Sanford et al. | |
| 5,451,514 A | 9/1995 | Boudet et al. | |
| 5,453,566 A | 9/1995 | Shewmaker et al. | |
| 5,459,252 A | 10/1995 | Conkling et al. | |
| 5,464,763 A | 11/1995 | Schilperoort et al. | |
| 5,478,744 A | 12/1995 | Sanford et al. | |
| 5,501,967 A | 3/1996 | Offringa et al. | |
| 5,530,196 A | 6/1996 | Fraley et al. | |
| 5,580,722 A | 12/1996 | Foulkes et al. | |
| 5,610,288 A | 3/1997 | Rubenstein | |
| 5,635,381 A | 6/1997 | Hooykaas et al. | |
| 5,665,543 A | 9/1997 | Foulkes et al. | |
| 5,668,295 A | 9/1997 | Wahab et al. | |
| 5,683,985 A | 11/1997 | Chu et al. | |
| 5,684,241 A | 11/1997 | Nakatani et al. ............ | 800/205 |
| 5,693,512 A | 12/1997 | Finer et al. | |

(Continued)

FOREIGN PATENT DOCUMENTS

CA 2032443 6/1991

(Continued)

OTHER PUBLICATIONS

Kim et al. 1994, Plant Molecular Biology 24: 105-117.*

(Continued)

*Primary Examiner*—Ashwin Mehta
*Assistant Examiner*—Li Zheng
(74) *Attorney, Agent, or Firm*—Myers, Bigel, Sibley & Sajovec, P.A.

(57) ABSTRACT

Putrescine-N-Methyltransferase promoters, particularly promoters isolated from tobacco, are disclosed, along with recombinant nucleic acids containing the same, expression vectors containing the same, and transgenic plants produced therewith. Methods of use thereof are also disclosed.

31 Claims, 1 Drawing Sheet

U.S. PATENT DOCUMENTS

| | | | |
|---|---|---|---|
| 5,713,376 A | 2/1998 | Berger | |
| 5,716,780 A | 2/1998 | Edwards et al. | |
| 5,723,751 A | 3/1998 | Chua | |
| 5,731,179 A | 3/1998 | Komari et al. | |
| 5,759,829 A | 6/1998 | Shewmaker et al. | |
| 5,767,378 A | 6/1998 | Bojsen et al. | |
| 5,776,502 A | 7/1998 | Foulkes et al. | |
| 5,776,771 A | 7/1998 | Yu et al. | |
| 5,830,728 A | 11/1998 | Christou et al. | |
| 5,834,236 A | 11/1998 | Lamb et al. | |
| 5,837,876 A | 11/1998 | Conkling et al. | |
| 5,843,720 A | 12/1998 | Tangney et al. | |
| 5,846,720 A | 12/1998 | Foulkes et al. | |
| 5,851,804 A | 12/1998 | Snyder et al. | |
| 5,858,742 A | 1/1999 | Fraley et al. | |
| 5,858,774 A | 1/1999 | Malbon et al. | |
| 5,863,733 A | 1/1999 | Foulkes et al. | |
| 5,877,023 A | 3/1999 | Sautter et al. | |
| 5,929,306 A | 7/1999 | Torisky et al. | |
| 5,932,782 A | 8/1999 | Bidney | |
| 5,962,768 A | 10/1999 | Cornelissen et al. | |
| 5,976,793 A | 11/1999 | Foulkes et al. | |
| 5,976,880 A | 11/1999 | Sautter et al. | |
| 5,981,839 A | 11/1999 | Knauf et al. | |
| 5,989,915 A | 11/1999 | Christou et al. | |
| 5,994,629 A | 11/1999 | Bojsen et al. | |
| 6,022,863 A | 2/2000 | Peyman | |
| 6,051,409 A | 4/2000 | Hansen et al. | |
| 6,051,757 A | 4/2000 | Barton et al. | |
| 6,060,310 A | 5/2000 | Cho-Chung | |
| 6,077,992 A | 6/2000 | Yadav | |
| 6,136,779 A | 10/2000 | Foulkes et al. | |
| 6,165,712 A | 12/2000 | Foulkes et al. | |
| 6,165,715 A | 12/2000 | Collins et al. | |
| 6,174,724 B1 | 1/2001 | Rogers et al. | |
| 6,203,976 B1 | 3/2001 | Foulkes et al. | |
| 6,255,560 B1 | 7/2001 | Fraley et al. | |
| 6,262,033 B1 | 7/2001 | Morishita et al. | |
| 6,271,031 B1 | 8/2001 | Falco et al. | |
| 6,281,410 B1 | 8/2001 | Knauf et al. | |
| 6,423,520 B1 | 7/2002 | Conkling et al. | |
| 6,586,661 B1 | 7/2003 | Conkling et al. | |
| 6,907,887 B2 | 6/2005 | Conkling | |
| 6,911,541 B2 | 6/2005 | Conkling et al. | |
| 2001/0006797 A1 | 7/2001 | Kumagai et al. | |
| 2001/0026941 A1 | 10/2001 | Held et al. | |
| 2002/0108151 A1 | 8/2002 | Conkling et al. | |
| 2003/0018997 A1 | 1/2003 | Conkling et al. | |
| 2003/0140366 A1 | 7/2003 | Conkling et al. | |
| 2004/0103454 A1 | 5/2004 | Conkling et al. | |
| 2004/0168211 A1 | 8/2004 | Conkling et al. | |
| 2006/0057723 A1 | 3/2006 | Conkling et al. | |

FOREIGN PATENT DOCUMENTS

| | | |
|---|---|---|
| CA | 2248622 | 3/1999 |
| CA | 2325344 | 10/1999 |
| CA | 1341091 | 9/2000 |
| EP | 0 116 718 B2 | 8/1984 |
| EP | 0 120 515 B1 | 10/1984 |
| EP | 0 120 516 B1 | 10/1984 |
| EP | 0 131 620 B1 | 1/1985 |
| EP | 0 131 623 B1 | 1/1985 |
| EP | 0 140 308 B2 | 5/1985 |
| EP | 0 159 779 B1 | 10/1985 |
| EP | 0 189 707 B1 | 8/1986 |
| EP | 0 224 287 A1 | 6/1987 |
| EP | 0 265 556 A1 | 5/1988 |
| EP | 0 270 822 A1 | 6/1988 |
| EP | 0 290 799 B1 | 11/1988 |
| EP | 0 290 799 B9 | 11/1988 |
| EP | 0 320 500 A2 | 6/1989 |
| EP | 0 176 112 B1 | 5/1990 |
| EP | 0 458 367 B1 | 11/1991 |
| EP | 0486214 | 11/1991 |
| EP | 0 467 349 B1 | 1/1992 |
| EP | 0 486 214 A2 | 5/1992 |
| EP | 0 486 234 B1 | 5/1992 |
| EP | 0 131 624 B1 | 9/1992 |
| EP | 0 223 399 B1 | 4/1994 |
| EP | 0 240 208 | 11/1994 |
| EP | 0 240 208 B1 | 11/1994 |
| EP | 0 647 715 A1 | 4/1995 |
| EP | 0 818 532 A1 | 1/1998 |
| EP | 1 457 562 A1 | 9/2004 |
| EP | 1 457 563 A1 | 9/2004 |
| WO | WO 84/02913 | 8/1984 |
| WO | WO 84/ 02919 | 8/1984 |
| WO | WO 84/ 02920 | 8/1984 |
| WO | WO 90/12084 | 10/1990 |
| WO | WO 91/01379 | 2/1991 |
| WO | WO 91/02070 | 2/1991 |
| WO | WO 91/11535 | 8/1991 |
| WO | WO 91/13992 | 9/1991 |
| WO | WO 92/15680 | 9/1991 |
| WO | WO 91/14790 | 10/1991 |
| WO | WO 92/18522 | 10/1992 |
| WO | WO 92/19732 | 11/1992 |
| WO | WO 93/05163 | 3/1993 |
| WO | WO 93/05646 | 4/1993 |
| WO | WO 93/14768 | 8/1993 |
| WO | WO 93/17116 | 9/1993 |
| WO | WO 94/20627 | 9/1994 |
| WO | WO 94/26913 | 11/1994 |
| WO | WO 9428142 | 12/1994 |
| WO | WO 95/11687 | 5/1995 |
| WO | WO 95/12415 | 5/1995 |
| WO | WO 95/16031 | 6/1995 |
| WO | WO 95/34668 | 12/1995 |
| WO | WO 95/35388 | 12/1995 |
| WO | WO 96/21725 | 7/1996 |
| WO | WO 97/05261 | 2/1997 |
| WO | WO 97/08330 | 3/1997 |
| WO | WO 97/12046 | 4/1997 |
| WO | WO 97/32016 | 9/1997 |
| WO | WO 97/38723 | 10/1997 |
| WO | WO 97/41892 | 11/1997 |
| WO | WO 97/44064 | 11/1997 |
| WO | WO 97/44450 | 11/1997 |
| WO | WO 97/49727 | 12/1997 |
| WO | WO 98/05757 | 2/1998 |
| WO | WO 99/10512 | 3/1998 |
| WO | WO 99/14348 | 3/1998 |
| WO | WO 99/25854 | 5/1998 |
| WO | WO 98/30701 | 7/1998 |
| WO | WO 98/32843 | 7/1998 |
| WO | WO 98/56923 | 12/1998 |
| WO | WO 99/26634 | 6/1999 |
| WO | WO 99/32619 | 7/1999 |
| WO | WO 99/32642 | 7/1999 |
| WO | WO 99/49029 | 9/1999 |
| WO | WO 99/53050 | 10/1999 |
| WO | WO 99/61631 | 12/1999 |
| WO | WO 00/12735 | 3/2000 |
| WO | WO 00/18939 | 4/2000 |
| WO | WO 00/29566 | 5/2000 |
| WO | WO 00/37060 | 6/2000 |
| WO | WO 00/37663 | 6/2000 |
| WO | WO 00/63398 | 10/2000 |
| WO | WO 0067558 | 11/2000 |
| WO | WO 01/09302 | 2/2001 |
| WO | WO 01/38514 | 5/2001 |
| WO | WO 01/44482 | 6/2001 |
| WO | WO 01/49844 | 7/2001 |

| | | |
|---|---|---|
| WO | WO 01/51630 | 7/2001 |
| WO | WO 01/68836 | 9/2001 |
| WO | WO 01/77350 | 10/2001 |
| WO | WO 02/00927 | 1/2002 |
| WO | WO 02/18607 | 3/2002 |

OTHER PUBLICATIONS

Oommenn et al 1994, The Plant Cell 6:1789-1803.*
Maniatis et al. *Science* 236:1237-1245 (1987).
Singer and Berg "Genes and Genomes" Section 3.2 pp. 134-145. University Science Books, Mill Valley, Calif. (1991).
Hibi et al. "Gene Expression in Tobacco Low-Nicotine Mutants" *The Plant Cell*: vol. 6, 723-735.
Shoji et al. "Jasmonate Induction of Putrescine N-Methltransferase Genes in the Root of *Nicotiana sylvestris*" *Plant Cell Physiol.* 41(7): 831-839 (2000).
Supplementary European Search Report, Application No. EP 01990934.0, dated Jul. 22, 2005, 3 pages.
Accession No. AC115109.2.1.59356.
Adams et al. "Biogenesis and Chemistry of Alkaloid-Derived N-Nitronsamines" 184th *American Chemical Society National Meeting* abstract #66 (1982).
Adams et al. "On the Pharmacokinetics of Tobacco-Specific N-Nitrosamines in Fischer Rats" *Carcinogenesis* vol. 6, pp. 509-511 (1985).
Adams et al. "Pharmacokinetics of Tobacco-Specific N-Nitrosamines" *World Health Organization International Agency for Research on Cancer Scientific Publications* No. 57, pp. 779-785 (1984).
Adams et al. "Tobacco-Specific *N*-Nitrosamines in Dry Snuff" *Fd Chem Toxic* 25(3): 245-246 (1987).
Adams et al. "Toxic and Carcinogenic Agents in Undiluted Mainstream Smoke and Sidestream Smoke of Different Types of Cigarettes" *Carcinogenesis* 8(5): 729-731 (1987).
Andersen et al. "Accumulation of 4-(*N*-Methyl-*N*-nitrosamino)-1-(3-pyridyl)-1-butanone in Alkaloid Genotypes of Burley Tobacco During Postharvest Processing: Comparisons with *N*-Nitrosonomicotine and Probable Nitrosamine Precursors" *Cancer Research* 45: 5287-5293 (1985).
Andersen et al. "Effect of Storage Conditions on Nitrosated, Acylated, and Oxidized Pyridine Alkaloid Derivatives in Smokeless Tobacco Products" *Cancer Research* 49: 5895-5900 (1989).
Andersen et al. "effects of Air-Curing Environment on Alkaloid-Derived Nitrosamines in Burely Tobacoo" *IARC Science Publication* 84: 451-455 (1987).
Andersen et al. "Levels of Alkaloids and Their Derivatives in Air- and Fire- Cured KY 171 Dark Tobacco During Prolonged Storage: Effects of Temperature and Moisture" *Tobacco Science* 34: 50-56 (1990).
Andersen et al. "N'-Acyl and N'-Nitroso Pyridine Alkaloids in Alkaloid Lines of Burely Tobacco During Growth and Air-Curing" *J Agric Food Chem* 37: 44-50 (1989).
Andersen et al. "pH Changes in Smokeless Tobaccos Undergoing Nitrosation" *ACS Symposium Series Nitrosamines and Related N-Nitroso Compounds* Chapter 29 pp. 320-321(1992).
Andersen et al. "Total Carbonyls and Phenols in Experimental Burely and Bright Tobacco" *J Agric Food Chem* 27(4): 891-895 (1979).
Atawodi et al. "Tobacco-Specific Nitrosamines in Some Nigerian Cigarettes" *Cancer Letters* 97: 1-6 (1995).
Bae et al. "The Nitrosation of Hexetidine and Hexedine: Characterization of the Major Nitrosamine from Common Antimicrobial Agents" *Chem Res Toxicol*7: 868-876 (1994).
Bandurski et al. "Hormone Synthesis and Metabolism: B1. Auxin Biosynthesis and Metabolism" *Plant Hormones* P.J. Davies (ed.) pp. 39-51 (1995).
Bhide et al. "Tobacco-Specific N-Nitrosamines [TSNA] in Green Mature and Processed Tobacco Leaves from India" *Beitrage zur Tabakforschung International* 14(1): 29-32 (1987).
Bhide et al. "Tobacco-Specific N-Nitrosamines in Green Mature Tobacco Leaves and Its Progressive Increase on Drying and Processing" (manuscript) Oct. 1985.

Blaszczyk et al. "Increased Resistance to Oxidative Stress in Transgenic Tobacco Plants Overexpressing Bacterial Serine Acetyltransferase" *The Plant Journal* 20(2): 237-243 (1999).
Brittebo et al. "Metabolism of Tobacco-Specific Nitrosamines by Cultured Rat Nasal Mucosa" *Cancer Research* 43: 4343-4348 (1983).
Brunnemann "Topics related to N-Nitrosamines and Their Precursors" 45th *TCRC* Oct. 20-23, 1991 Asheville, NC.
Brunneman et al. "Analytical Studies on N-Nitrosamines in Tobacco and Tobacco Smoke" *Recent Advances in Tobacco Science* vol. 17 pp. 71-112 (1991).
Brunnemann et al. "Analytical Studies on Tobacco-Specific N-Nitrosamines in Tobacco and Tobacco Smoke" *Critical Reviews in Toxicology* 21(4): 235-240 (1991).
Brunnemann et al. "Assessment of the Carcinogenic N-Nitrosodiethanolamine in Tobacco products and Tobacco Smoke" *Carcinogenesis* 2(11): 1123-1127 (1981).
Brunnemann et al. "Identification and Analysis of a New Tobacco-Specific N-nitrosamine, 4-(methylnitrosamino)-4-(3-pyridyl)-1-butanol" *Carcinogenesis* 8(3): 465-469 (1987).
Brunnemann et al. "Isolation, Identification and Bioassay of the Tobacco-Specific N-Nitrosamine, 4-(methylnitrosamino)-4-(3-Pyridyl)-1-Butanol" *Seventy-Ninth Annual Meeting of the American Association for Cancer Research* vol. 29, abstract 332 (1988).
Brunnemann et al. "N-Nitrosamines in Chewing Tobacco: An International Comparison" *J Agric Food Chem* 33:1178-1181 (1985).
Brunnemann et al. "N-Nitrosamines: Environmental Occurrence, in Vivo Formation and Metabolism" 183rd *American Chemical Society National Meeting* abstract 34 (1982).
Brunnemann et al. "N-Nitrosamines: Environmental Occurrence, in Vivo Formation and Metabolism" *J Toxicology—Clinical Toxicology* 19(6&7): 661-688 (1982-83).
Brunnemann et al. "N-Nitrosodiethanolamine in Tobacco and Mainstream and Sidestream Smoke" *World Health Organization Environmental Carcinogens Selected Methods of Analysis* vol. 6 pp. 85-92 (1983).
Brunnemann et al. "Role of Tobacco Stems in the Formation of N-Nitrosamines in Tobacco and Cigarette Mainstream and Sidestream Smoke" *J Agric Food Chem* 31: 1221-1224 (1983).
Burton et al. "Accumulation of Tobacco-Specific Nitrosamines During Curing and Aging of Tobacco" *American Chemical Society Symposium Series: Nitrosamines and Related N-Nitroso Compounds* Chapter 41 pp. 361-362 (1992).
Burton et al. "Changes in Chemical Composition of Burely Tobacco During Senescence and Curing 2. Acylated Pyridine Alkaloids" *J Agric Food Chem* 36: 579-584 (1988).
Burton et al. "Changes in Chemical Composition of Burely Tobacco During Senescence and Curing 3. Tobacco-Specific Nitrosamines" *J Agric Food Chem* 37: 427-430 (1989).
Burton et al. "Changes in Chemical Composition of Tobacco Lamina During Senescence and Curing 1. Plastid Pigments" *J Agric Food Chem* 33; 879-883 (1985).
Burton et al. "Distribution of Tobacco Constituents in Tobacco Leaf Tissue 1. Tobacco-Specific Nitrosamines, Nitrate, and Nitrite and Alkaloids" *J Agric Food Chem* 40: 1050-1055 (1992).
Burton et al. "Distribution of Tobacco Constituents in Tobacco Leaf Tissue 1. Tobacco-Specific Nitrosamines, Nitrate, Nitrite and Alkaloids" slides reprint from *J Agric Food Chem* vol. 40 (1992).
Burton et al. "Influence of Temperature and Humidity on the Accumulation of Tobacco-Specific Nitrosamines in Stored Burely Tobacco" *J Agric Food Chem* 37: 1372-1377 (1989).
Burton et al. "Relationship Between Tobacco-Specific Nitrosamines and Nitrite from Different Air-Cured Tobacco Varieties" *J Agric Food Chem* 42: 2007-2011 (1994).
Burton et al. "The Effects of Harvesting and Curing Procedures on the Composition of the Cured Leaf" *Tobacco Science* vol. 5 pp. 49-53 (1963).
Bush et al. "Origin of Nitrite-Nitrogen for Tobacco-Specific *N'*-Nitrosamine Formation" *Technologie-Agriculture*, No. 9814, p. 139 (1995).
Carmella et al. "Formation of Hemoglobin Adducts upon Treatment of F344 Rats with the Tobacco-specific Nitrosamines 4-(Methylnitrosamino)-1-(3-pyridyl)-1-butanone and N'-Nitrosonomicotine" *Cancer Research* 47: 2626-2630 (1987).
Carmella et al. "Mass Spectrometric Analysis of Tobacco-Specific Nitrosamine Hemoglobin Adducts in Snuff Dippers, Smokers, and Nonsmokers" *Cancer Research* 50: 5438-5445 (1990).
Carmella et al. "Metabolites of the Tobacco-Specific Nitrosamine 4-(Methylnitrosamino)-1-(3-pyridyl)-1-butanone in Smokers' Urine" *Cancer Research* 53: 721-724 (1993).
Carter et al. "Tobacco Nectarin V Is a Flavin-Containing Berberine Bridge Enzyme-Like Protein with Glucose Oxidase Activity" *Plant Physiology* 134: 460-469 (2004).
Castonguay et al. "Carcinogenicity, Metabolism and DNA Binding of the Tobacco Specific Nitrosamine, 4-(Methylnitrosamino)1-(3-Pyridyl)-1-Butanone (NNK)" *Seventy-Second Annual Meeting of the American Association for Cancer Research* abstract 297 (1981).
Castonguay et al. "Metabolism of Tobacco-Specific Nitrosamines in Cultured Human Tissues" *Seventy-Third Annual Meeting of the American Association for Cancer Research* vol. 23, abstract 333 (1982).
Chamberlain et al. "Chemical Composition of Nonsmoking Tobacco Products" *J Agric Food Chem* 36: 48-50 (1988).
Chamberlain et al. "Curing Effects on Contents of Tobacco Specific Nitrosamines in Bright and Burley Tobaccos" 41st TCRC #53 (1987).
Chamberlain et al. "Effects of Curing and Fertilization on Nitrosamine Formation in Bright and Burley Tobacco" *Beitrage zur Tabakiorschung International* 15(2): 87-92 (1992).
Chamberlain et al. "Studies on the Reduction of Nitrosamines in Tobacco" *Tobacco Science* 38-39: 81-82 (1985).
Chang et al. "Gene Expression from Both Intronless and Intron-Containing Rous Sarcoma Virus Clones is Specifically Inhibited by Anti-Sense RNA" *Molecular and Cellular Biology* 5(9): 2341-2348 (1985).
Chaplin et al. "Catalog of the Tobacco Introductions in the U.S. Department of Agriculture's Tobacco Germplasm Collection (*Nicotiana tabacum*)" *U.S. Department of Agriculture, Agricultural Reviews and Manuals* (1982).
Chintapakorn et al. "Antisense-mediated Down-regulation of Putrescine N-methyltransferase Activity in Transgenic *Nicotiana tabacum*L. Can Lead to Elevated Levels of Anatabine at the Expense of Nicotine" *Plant Molecular Biology* 53: 87-105 (2003).
Creelman et al. "Involvement of a Lipoxygenase-Like Enzyme in Abscisic Acid Biosynthesis" *Plant Physiology* 99: 1258-1260 (1992).
DeBardeleben "Virginia Tobacco" *Dictionary of Tobacco Terminology* p. 93.
DeBlock et al. "Expression of Foreign Genes in Regenerated Plants and in Their Progeny" *EMBO Journal* 3(8): 1681-1689 (1984).
Dewick "Alkaloids" *Medicinal Natural Products: A Biosynthetic Approach* Chapter 6, John Wiley & Sons (1997).
Djordjevic "Tobacco-Specific nitrosamine Accumulation in Different Genotypes of Burely Tobacco at Different Stages of Growth and Air-Curing" 41st *Tobacco Chemists' Research Conference* 36 pages (1987).
Djordjevic et al. "Accumulation and Distribution of Acylated Nomicotine Derivatives in Flue-Cured Tobacco Alkoloid isolines" *J Agric Food Chem* 38: 347-350 (1990).
Djordjevic et al. "Assessment of Major Carcinogens and Alkaloids in the Tobacco and Mainstream Smoke of USSR Cigarettes" *Int J Cancer* 47: 348-351 (1991).
Djordjevic et al. "The Need for Regulation of Carcinogenic N-Nitrosamines in Oral Snuff" *Fd Chem Toxic* 31(7): 497-501 (1993).
Djordjevic et al. "Tobacco-Specific Nitrosamine Accumulation and Distribution in Flue-Cured Tobacco Alkaloid Isolines" *J Agric Food Chem* 37: 752-756 (1989).
Doerr-O'Rourke et al. "Effect of Phenethyl Isothiocyanate on the Metabolism of the Tobacco-Specific Nitrosamine 4-(methylnitrosamino)-1-(3-pyridyl)-1-butanone by Cultured Rat Lung Tissue" *Carcinogenesis* 12(6): 1029-1034 (1991).

Elomaa et al. "Transformation of Antisense Constructs of the Chalcone Synthase Gene Superfamily into *Gerbera hybrida*: Differential Effect on the Expression of Family members" *Molecular Breeding* 2:41-50 (1996).
Engelberth et al. "Ion Channel-Forming Alamethicin is a Potent Elicitor of Volatile Biosynthesis and Tendril Coiling. Cross Talk Between Jasmonate and Salicylate Signaling in Lima Bean" *Plant Physiology* 125: 369-377 (2001).
Feth et al. "Determination of Putrescine N-methyltransferase By High Performance Liquid Chromatography" *Phytochemistry* 24(5): 921-923 (1985).
Feth et al. "Regulation in Tobacco Callus of Enzyme Activities of the Nicotine Pathway I. The Route Ornithine to Methylpyrroline"*Chemical Abstracts* 105: 112144 (1986) (Abstract).
Finster "Literature Study: N-Nitrosamines in Tobacco Products" (1986).
Fischer et al. "Exposure to Tobacco Specific Nitrosamines by the Different Habits of Tobacco Use, Examination of Transfer Rates and the Influence of Smoking Habits" *Tobacco Specific Nitrosamines* <http://www.dkfz-heidelberg.de/tox/tsna.htm> accessed on Feb. 14, 2001. 3 pages.
Fischer et al. "Improved Method for the Determination of Tobacco-Specific Nitrosamines (TSNA) in Tobacco Smoke" *Beitrage zur Tabakforschung International* 14(3): 145-153 (1989).
Fischer et al. "Influence of Smoking Parameters on the Delivery of Tobacco-Specific Nitrosamines in Cigarette Smoke—A Contribution to Relative Risk Evaluation" *Carcinogenesis* 10(6): 1059-1066 (1989).
Fischer et al. "Investigations on the Origin of Tobacco-Specific Nitrosamines in Mainstream Smoke of Cigarettes" *Carcinogenesis* 11(5): 723-730 (1990).
Fischer et al. "No Pyrosynthesis of N'-Nitrosonomicotine (NNN) and 4-(Methylnitrosamino)-1-(3-Pyridyl)-1-butanone (NNK) from Nicotine" *Effects of Nicotine on Biological Systems: Advances in Pharmacological Sciences* pp. 103-107.
Fischer et al. "Preformed Tobacco-Specific Nitrosamines in Tobacco—Role of Nitrate and Influence of Tobacco Type" *Carcinogenesis* 10(8): 1511-1517 (1989).
Fischer et al. "Tobacco-Specific Nitrosamines in Canadian Cigarettes" *J Cancer Res Clin Oncol* 116: 563-568 (1990).
Fischer et al. "Tobacco-Specific Nitrosamines in Commercial Cigarettes: Possibilities for Reducing Exposure" *Relevance to Human Cancer of N-Nitroso Compounds, Tobacco Smoke and Mycotoxins* pp. 489-492 (1991).
Fischer et al. "Tobacco-Specific Nitrosamines in European and USA Cigarettes" *Archiv fur Geschwulstforschung* 60: 169-177 (1990).
Fischer et al. "Tobacco-Specific Nitrosamines in Mainstream Smoke of West German Cigarettes—Tar Alone is Not a Sufficient Index for the Carcinogenic Potential of Cigarette Smoke" *Carcinogenesis* 10(1): 169-173 (1989).
Foiles et al. "Mass Spectrometric Analysis of Tobacco-Specific Nitrosamine-DNA Adducts in Smokers and Nonsmokers" *Chem Res Toxicol*4: 364-368 (1991).
Fung et al. "Spray Damage and Residue Levels in Tobacco Treated with Various Concentrations of 2, 4-D at Different Stages of Growth" *Australian Journal of Experimental Agriculture and Animal Husbandry* 13: 328-338 (1973).
Gondwe et al. "Screening Tobacco Types, Cultivars and Curing Methods for Low Nitrosamine Tobacco Production in Malawi" *Agricultural Research and Extension Trust 1998 Coresta Congress at Yokohama*, Japan 7 pages.
Hamill et al. "Over-Expressing a Yeast Ornithine Decarboxylase Gene in Transgenic Roots of *Nicotiana rstica* Can Lead to Enhanced Nicotine Accumulation" *Plant Molecular Biology* 15: 27-38 (1990).
Hecht et al. "Cyclic and Tobacco-Specific Nitrosamines: Metabolism and Macromolecular Adduct Formation" *Abstracts of Papers:* 204th *American Chemical Society Meeting* abstract 68 (1992).
Hecht et al. "Endogenous Nitrosation of Tobacco Alkaloids in Rats" *Abstracts of Papers:* 212th *American Chemical Society Meeting* abstract 64 (1996).
Hecht et al. "Evidence for 4-(3-pyridyl)-4-oxobutylation of DNA in F344 Rats Treated with the Tobacco-Specific Nitrosamines 4-(methylnitrosamino)-1-(3-pyridyl)-1-butanone and N'-nitrosonornicotine" *Carcinogenesis* 9(1): 161-165 (1988).
Hecht et al. "HPLC-TEA of Tobacco-Specific Nitrosamines" *World Health Organization: Environmental Carcinogens Selected Methods of Analysis* H. egan (ed) 6: 429-436 (1983).
Hect et al. "Induction of Oral Cavity Tumors in F344 Rats by Tobacco-Specific Nitrosamines and Snuff" *Cancer Research* 46: 4162-4166 (1986).
Hect et al. "Metabolism of the Tobacco-Specific Nitrosamine 4-(methylnitrosamino)-1-(3-pyridyl)-1-butanone in the Patas Monkey: Pharmacokinetics and Characterization of Glucuronide Metabolites" *Carcinogenesis* 14(2); 229-236 (1993).
Hecht et al. "Reaction of Nicotine and Sodium Nitrite: Formation of Nitrosamines and Fragmentation of the Pyrrolidine Ring" *J Organic Chemistry* 43(1): 72:76 (1978).
Hecht et al. "Recent Studies on the Metabolic Activation of Tobacco-Specific Nitrosamines" *Abstracts of Papers Part 1: 217th American Chemical Society National Meeting* abstract 012 (1999).
Hecht et al. "The Metabolism of Cyclic Nitrosamines" N-*Nitroso Compounds* ACS Symposium Series 174 pp. 49-75 (1981).
Hecht et al. "The Relevance of Tobacco-Specific Nitrosamines to Human Cancer" *Cancer Surveys* 8(2): 273-294 (1989).
Hecht et al. "Tobacco-Specific Nitrosamine Adducts: Studies in Laboratory Animals and Humans" *Environmental Health Perspectives* 99: 57-63 (1993).
Hecht et al. "Tobacco-Specific Nitrosamines in Tobacco and Tobacco Smoke" *World Health Organization: Environmental Carcinogens Selected Methods of Analysis* H. Egan (ed) 6: 93-101 (1983).
Hecht et al. "Tobacco-specific Nitrosamines, and Important Group of Carcinogens in Tobacco and Tobacco Smoke" *Carcinogenesis* 9(6): 875-884 (1988).
Hecht et al. "Tobacco-Specific Nitrosamines: Formation from Nicotine in Vitro and During Tobacco Curing and Carcinogenicity in Strain A Mice" *J Natl Cancer Inst* 60(4): 819-824 (1978).
Hecht et al. "Tobacco-Specific Nitrosamines: Occurrence, Formation, Carcinogenicity and Metabolism" *Accounts of Chemical Research* 12: 92-98 (1979).
Hecht et al. "2'-Hydroxylation of Nicotine by Cytochrome P450 2A6 and Human Liver Microsomes: Formation of a Lung Carcinogen Precursor" *PNAS* 97(23): 12493-12497 (2000).
Hecht et al. "A Study of Tobacco Carcinogenesis XLII. Bioassay in A/J Mice of Some Structural Analogues of Tobacco-Specific Nitrosamines" *Cancer Letters* 42: 141-145 (1988).
Hecht et al. "Biochemistry, Biology and Carcinogenicity of Tobacco-Specific N-Nitrosamines" *Chemical Research in Toxicology* 11(6): 560-603 (1998).
Hecht et al. "Biomarkers for Human Uptake and Metabolic Activation of Tobacco-Specific Nitrosamines" *Cancer Research (supplemental)* 54: 1912s-1917s (1994).
Hecht et al. "Chemical Studies on Tobacco Smoke. XXXIII. N'-Nitrosonornicotine in Tobacco: Analysis of Possible Contributing Factors and Biologic Implications" *Journal of the National Cancer Institute* 54(5): 1237-1244 (1974).
Hecht et al. "Comparative Carcinogenicty in F344 Rats of the Tobacco-specific Nitrosamines, N'-Nitrosonornicotine and 4-(N-Methyl-N-nitrosamino)-1-(3-pyridyl)-1-butanone" *Cancer Research* 40: 298-302 (1980).
Hecht et al. "Comparative Carcinogenicity of o-Toluidine Hydrochloride and 0-Nitrosotolune in F-344 Rats" *Cancer Letters* 16: 103-108 (1982).
Hecht et al. "DNA Adduct Formation from Tobacco-Specific N-Nitrosamines" *Mutation Research* 424: 127-142 (1999).
Heeschen et al. "Nicotine Stimulates Angiogenesis and Promotes Tumor Growth and Atherosclerosis" *Nature Medicine* 7(7):833-839 (2001).
Hoffmann et al. "Assessment of Tobacco-Specific N-Nitrosamines in Tobacco Products" *Cancer Research* 39: 2505-2509 (1979).
Hoffmann et al. "Carcinogenic Tobacco-specific N-Nitrosamines in Snuff and in the Saliva of Snuff Dippers" *Cancer Research* 41: 4305-4308 (1981).
Hoffmann et al. "Chemical Studies on Tobacco Smoke. XXVI. On the Isolation and Identification of Volatile and Non-Volatile N-Nitrosamines and Hydrazines in Cigarette Smoke" *Int Agency Res Cancer Publ* 9: 159-165 (1974).
Hoffmann et al. "Formation and Analysis of N-Nitrosamines in Tobacco Products and Their Endogenous Formation in Consumers" *N-Nitroso Compounds: Occurrence, Biological Effects and Relevance to Human Cancer*, World Health Organization, Proceedings of the VIIIth International Symposium on N-Nitroso Compounds, pp. 743-762 (1983).
Hoffmann et al. "Formation of Tobacco-Specific Nitrosamines: Carcinogenicity and Role of Dietary Fat in Their Carcinogenicity" *Nitrosamines and Related N-Nitroso Compounds* chapter 21, pp. 267-278 (1994).
Hoffmann et al. "Formation of Tobacco-Specific N-Nireosamines, Their Carcinogenicity and the Role of Dietary Fat in their Carcinogenicity" *Abstracts of Papers: 204th American Chemical Society National Meeting* abstract 119 (1992).
Hoffman et al. "Formation, Occurrence and Carcinogenicity of N-Nitrosamines in Tobacco Products" *Abstracts of Papers: 181st American Chemical Society National Meeting* abstract 59 (1981).
Hoffmann et al. "GC-TEA of Volatile Nitrosamines from Tobacco Products" *World Health Organization Environmental Carcinogens Selected Methods of Analysis* vol. 6, pp. 363-366 (1983).
Hoffmann et al. "Introduction: Tobacco-Specific N-Nitrosamines (TSNA)" *Critical Reviews in Toxicology* 21(4) (1991).
Hoffmann et al. "Nicotine: A Precursor for Carcinogens" *Cancer Letters* 26: 67-75 (1985).
Hoffmann et al. "Nicotine-Derived N-Nitrosamines (TSNA) and Their Relevance in Tobacco Carcinogenesis" *Critical Reviews in Toxicology* 21(4): 305-311 (1991).
Hoffmann et al. "Nicotine-Derived N-Nitrosamines and Tobacco-Related cancer: Current Status and Future Directions" *Cancer Research* 45: 935-944 (1985).
Hoffmann et al. "On the Endogenous Formation of N-Nitrosamines in Cigarette Smokers" *Seventy-Fourth Annual Meeting of the American Association for Cancer Research* vol. 24, abstract 241 (1983).
Hoffmann et al. "Origin in Tobacco Smoke of N'-Nitrosonornictoine, a Tobacco-Specific Carcinogen: *Brief Communication*" *J Natl Cancer Inst* 58(6): 1841-1844 (1977).
Hoffmann et al. "The Role of Volatile and Non volatile N-Nitrosamines in Tobacco Carcinogenesis" pp. *Banbury Report, vol. 3: A Safe Cigarette* Gori and Bock, editors. Cold Spring Harbor Laboratory. pp. 113-127 (1980).
Hoffmann et al. "Tobacco and Tobacco Smoke (Volatile and Tobacco-Specific Nitrosamines): General Aspects" *World Health Organization Environmental Carcinogens Selected Methods of Analysis* vol. 6, pp. 63-67 (1983).
Hoffmann et al. "Tobacco Specific N-Nitrosamines: Occurrence and Bioassays" *N-Nitroso Compounds: Occurrence and Biological Effects* World Health Organization, Proceedings of the VIIth International Symposium on N-Nitroso Compounds pp. 309-318 (1981).
Hoffmann et al. "Tobacco-Specific N-Nitrosamines and Areca-Derived N-Nitrosamines: Chemistry, Biochemistry, Carcinogenicity, and Relevance to Humans" *Journal of Toxicology and Environmental Health* 41: 1-52 (1994).
Hoffmann et al. "Volatile Nitrosamines in Tobacco and Mainstream and Sidestream Smoke and Indoor Environments" *World Health Organization Environmental Carcinogens Selected Methods of Analysis* vol. 6, pp. 69-83 (1983).
Irwin "Comments on a Recent Paper by Fischer and Co-Workers Entitled 'Tobacco-Specific Nitrosamines in Canadian Cigarettes'" British-American Tobacco Company Memo, 10 pages <http://www.health.gov.bc.ca/guildford/html/012/00001245.html> (1991).
Johnson et al. "N-Nitrosamines in Smoke Condensate from Several Varieties of Tobacco" *Journal of the National Cancer Institute* 48(6): 1845-1847 (1972).
JSC Matuco "General Tobacco Information" <http://www.jsc-matuco.ru/about.html> 4 pages, accessed on Dec. 4, 2002.
Kahl et al. "Herbivore-induced Ethylene Suppresses a Direct Defense but Not a Putative Indirect Defense Against and Adapted Herbivore" *Planta* 210: 336-342 (2000).
Kolomiets et al. "Lipoxygenase is Involved in the Control of Potato Tuber Development" *The Plant Cell* 13: 613-626 (2001).

Kumar et al. "Tobacco-Specific N-Nitrosamines in Tobacco and Mainstream Smoke of Indian Cigarettes" *Fd Chem Toxic* 29(6): 405-407 (1991).

Lagrimini et al. "Peroxidase-Induced Wilting in Transgenic Tobacco Plants" *The Plant Cell* 2: 7-18 (1990).

Larsson et al. "Polycyclic Aromatic Hydrocarbons and Volatile N-Nitrosamines in Some Dried Agricultural Products" *Swedish J Agric Res* 20(2): 49-56 (1990).

Liszewska et al. "Modification of Non-Protein Thiols Contents in Transgenic Tobacco Plants Producing Bacterial Enzymes of Cysteine Biosynthesis Pathway" *Acta Biochimica Polonica* 48(3): 647-656 (2001).

MacKown et al. "Tobacco-Specific N-Nitrosamines: Effect of Burley Alkaloid Isolines and Nitrogen Fertility Management" *J Agric Food Chem* 32: 1269-1272 (1984).

MacKown et al. "Tobacco-Specific N-Nitrosamines: Formation During Processing of Midrib and Lamina Fines" *J Agric Food Chem* 36: 1031-1035 (1988).

Maksymowicz et al. "Dealing with Chemical Injury to Tobacco" Online Publications AGR-158 <http://www.ca.uky.edu/agc/pubs/agr/agr158/agr158.htm> 3 pages, accessed on Sep. 16, 2005.

McCoy et al. "Influence of Chronic Ethanol Consumption on the Metabolism and carcinogenicity of Tobacco-Related Nitrosaminse" *World Health Organization N-Nitroso compounds: Occurrence and Biological Effects* Proceedings of the VIIth International Symposium on N-Nitroso Compounds in Tokyo pp. 635-642 (1981).

Melikian et al. "Volatile Nitrosamines: Analysis in Breast Fluid and Blood of Non-Lactating Women" *Fd Cosmet Toxicol* 19: 757-759 (1981).

Mingwu et al. "Effect of Maleic Hydrazide Application on Accumulation of Tobacco-Specific Nitrosamines in Air-Cured Burely Tobacco" *J Agric Food Chem* 42: 2912-2916 (1994).

Mirvish et al. "Ascorbate-Nitrite Reaction: Possible Means of Blocking the Formation of Carcinogenic N-Nitroso Compounds" *Science* 177: 65-68 (1972).

Mitacek et al. "Volatile Nitrosamines and Tobacco-Specific Nitrosamines in the Smoke of Thai Cigarettes: A Risk Factor for Lung Cancer and a Suspected Risk Factor for Liver Cancer in Thailand" *Carcinogenesis* 20(1): 133-137 (1999).

Mizusaki et al. "Phytochemical Studies on Tobacco Alkaloids XIV. The Occurence and Properties of Putrescine N-methyltransferase in Tobacco Roots" *Plant & Cell Physiology* 12: 633-640 (1971).

Nair et al. "Carcinogenic Tobacco-Specific Nitrosamines in Indian Tobacco Products" *Chem Toxic* 27(11): 751-753 (1989).

Napoli et al. "Introduction of a Chimeric Chalcone Synthase Gene into Petunia Results in Reversible Co-Suppression of Homologous Genes in trans" *The Plant Cell* 2: 279-289 (1990).

Nesmith "Actigard—A new Blue Mold Control Tool" *Reprint Tobacco Disease Article from KY Pest News*<http://www.uky.edu/Ag/kpn/kyblue/kyblu04/related/rtd0102.htm> 3 pages, no date.

Osterdahl et al. "N-Nitrosamines in Snuff and Chewing Tobacco on the Swedish Market in 1983" *Food Additives and Contaminants* 1(4): 299-305 (1984).

Osterdahl et al. "Volatile N-Nitrosamines in Snuff and Chewing Tobacco on the Swedish Market" *Fd Chem Toxic* 21(6): 759-762 (1983).

Peele et al. "Formation of Tobacco Specific Nitrosamines in Flue-Cured Tobacco" *Rec Adv Tobacco Sci* 27:3-12 (2001).

Perini "Experimental Cigarette Tobacco Column Tobacco Specific Nitrosamine (TSNA) Concentrations: A Comparison Among Single Blend Component Cigarettes and the No. 1580 Control Cigarette" Memo (1989).

Peterson et al. "Formation of NADP (H) Analogs of Tobacco-Specific Nitrosamines in Rat Liver and Pancreatic Microsomes" *Chem Res Toxicol* 7: 599-608 (1994).

Peterson et al. "Quantitation of Microsomal α-Hydroxylation of the Tobacco-specific Nitrosamine, 4-(Methylnitrosamino)-1-(3-pyridyl)-1-butanone" *Cancer Research* 51: 5495-5500 (1991).

Preston et al. "Tobacco Mosaic Virus Inoculation Inhibits Wound-Induced Jasmonic Acid-Mediated Responses Within But Not Between Plants" *Planta* 209: 87-95 (1999).

Preston-Martin "Evaluation of the Evidence That Tobacco-Specific Nitrosamines (TSNA) Cause Cancer in Humans" *Toxicology* 21(4): 295-298 (1991).

Prokopczyk et al. "Significance of Nitrosamines in Betel Quid Carcinogenesis" *ACS Symposium Series* 553, 204th *National Meeting of the American Chemical Society* chapter 43, Jan. 31, 1994.

Prokopczyk et al. "Supercritical Fluid Extraction in the Determination of Tobacco-Specific N-Nitrosamines in Smokeless Tobacco" *Chem Res Toxicol* 5: 336-340 (1992).

Reed Characterization of the A/B Regulon in Tobacco (*Nicotiana tabacum*) Thesis, Virginia Polytechnic Institute and State University (2003).

Renaud et al. "Tobacco-Specific Nitrosamines 940400-940600" *Research and Developmental, Neuchatel—Quaterly Report* 15 pages (1994).

Rivenson et al. "A Study of Tobacco Carcinogenesis XLIV. Bioassay in A/J Mice of Some N-Nitrosamines" *Cancer Letters* 47: 111-114 (1989).

Rivenson et al. "Carcinogenicity of Tobacco-Specific N-Nitrosamines (TSNA): The Role of the Vascular Network in the Selection of Target Organs" *Toxicology* 21(4): 255-264 (1991).

Rivenson et al. "Induction of Lung and Exocrine Pancreas Tumors in F344 Rats by Tobacco-specific and Areca-derived N-Nitrosamines" *Cancer Research* 48: 6912-6917 (1988).

Rivenson et al. "Observations on Lung Tumors Arising from Metaplastic Squamous Epithelium in Rats Treated Chronically With the Tobacco-Specific Nitrosamines, 4-(Methylnitrosamino)-1-(3-Pyridyl)-1-Butanone (NNK)" *Proceedings of the Seventy-Ninth Annual Meeting of the American Association for Cancer Research* vol. 29 Abstract 342 (1988).

Rivenson et al. "Pathogenetic Considerations on Nasal Cavity Tumors Induced by Tobacco Specific Nitrosamines (TSNA) in Rats" *European Journal of Cancer & Clinical Oncology* Abstract pp. 1312 (1983).

Rothstein et al. "Stable and heritable Inhibition of the Expression of Nopaline Synthase in Tobacco Expressing Antisense RNA" *Proceedings of the National Academy of Science, USA* 84: 8439-8443 (1987).

Ruhl et al. "Chemical Studies on Tobacco Smoke LXVI. Comparative Assessment of Volatile and Tobacco-Specific N-Nitrosamines in the Smoke of Selected Cigarettes from the U.S.A., West Germany, and France." *Journal of Analytical Toxicology* 4: 255-259 (1980).

Sachan "Identification of Signaling Factors Involved in the Regulation of Alkaloid Metabolism in *N. Tabacum*" Dissertation, University of Kentucky (2004).

Saunders "Effect of Regenerated Roots and Shoots on Nicotine Production in Tobacco Tissue Culture" *Drug Information Journal* 32:609-617 (1998).

Saunders et al. "Nicotine Biosynthetic Enzyme Activities in *Nicotiana tabacum* L. Genotypes with Different Alkaloid Levels" *Plant Physiol* 64: 236-240 (1979).

Schaller et al. "Enzymes of the Biosynthesis of Octadecanoid-Derived Signaling Molecules" *Journal of Experimental Botany* 52(354): 11-23 (2001).

Schmeltz et al. "Nitrogen-Containing Compounds in Tobacco and Tobacco Smoke" *Chemical Reviews* 77(3): 295-311 (1977).

Schweizer et al. "Jasmonate-Inducible Genes Are Activated in Rice By Pathogen Attack Without a Concomitant Increase in Endogenous Jasmonic Acid Levels" *Plant Physiology* 114: 79-88 (1997).

Shoji et al. "Expression Patterns Of Two Tobacco Isoflavone Reductase-Like Genes And Their Possible Roles In Secondary Metabolism In Tobacco" *Plant Molecular Biology* 50: 427-440 (2002).

Sircar et al. "Soybean Lipoxygenase Inhibition by Nonsteroidal Anti-inflammatory Drugs" *Prostaglandins* 25(3): 939-396 (1983).

Sitbon et al. "Expression of Auxin-Inducible Genes in Relation to Endogenous Indoleacetic Acid (IAA) Levels in Wild-Type and IAA-Overproducing Transgenic Tobacco Plants" *Physiologia Plantarum* 98: 677-684 (1996).

Sitbon et al. "Transgenic Tobacco Plants Coexpressing the *Agrobacterium tumefaciens iaaM* and *iaaH* Genes Display Altered growth and Indoleacetic Acid Metabolism" *Plant Physiology* 99: 1062-1069 (1992).

Smith et al. "Antisense RNA Inhibition of Polygalacturonase Gene Expression in Transgenic Tomatoes" *Nature* 334: 724-334 (1988).

Spiegelbalder et al. "A Method for the Determination of Tobacco-specific Nitrosamines (TSNA), Nitratie and Nitrite in Tobacco Leaves and Processed Tobacco" *Beitrage zur Tabakforschung International* 14(3): 135-144 (1989).

Spiegelhalder et al. "Tobacco-Specific Nitrosamines" *European Journal of Cancer Prevention* 5(suppl. 1): 33-38 (1996).

Splegelhalder et al. "Formation of Tobacco-Specific Nitrosamines" *Critical Reviews in Toxicology* 20(64): 241 (1991).

Staswick et al. "C2. Jasmonates, Salicyclic Acid and Brassinolides. C2a. Jasmonate Activity in Plants." *Plant Hormones: Physiology, Biochemistry and Molecular Biology* pp. 179-187, Davies, ed. Kluwer Academic Publishers (1995).

Stedman et al. "The Chemical Composition of Tobacco and Tobacco Smoke" *Chemical Reviews* 68: 153-207 (1968).

Thornburg et al. "Wounding *Nicotiana tabacum* Leaves Causes a Decline in Endogenous Indole-3-Acetic" *Plant Physiol* 96: 802-805 (1991).

Tricker et al. "The Occurrence of *N*-Nitro Compounds in Zarda Tobacco" *Cancer Letters* 42: 113-118 (1988).

Tricker et al. "The Occurrence of Tobacco-Specific Nitrosamines in Oral Tobacco Products and Their Potential Formation Under Simulated Gastric Conditions" *Fd Chem Toxic* 26(10): 861-865 (1988).

Trushin et al. "Stereoselective Metabolism of Nicotine and Tobacco-Specific *N*-Nitrosamines to 4-Hydroxy-4-(3-pyridyl) butanoic Acid in Rats" *Chem Res Toxicol* 12: 164-171 (1999).

Tso "Organic Metabolism—Alkaloids" *Production, Physiology, and Biochemistry of Tobacco Plant* pp. 467-486 IDEALS, Inc. (1990).

Tso "The Locki of Alkaloid Formation" *Physiology and Biochemistry of Tobacco Plants* pp. 233-235, Dowden, Hutchinson & Ross, Inc. (1972).

Uknes et al. "Acquired Resistance in Arabidopsis" *The Plant Cell* 4: 645-656 (1992).

Upadhaya et al. "Preparation of Pyridine-*N*-glucuronides of Tobacco-Specific Nitrosamines" *Chem Res Toxicol* 14: 555-561 (2001).

Wagner et al. "The Pyridine-Nucleotide Cycle in Tobacco Enzyme Activities for the De-Novo Synthesis of NAD" *Planta* 165: 532-537 (1985).

Wagner et al. "The Regulation of Enzyme Activities of the Nicotine Pathway in Tobacco" *Physiol Plantarum* 68: 667-672 Copenhagen (1986).

Walling et al. "The Myriad Plant Responses to Herbivores" *J Plant Growth Regul* 19: 195-216 (2000).

Waterhouse et al. "Virus Resistance and Gene Silencing: Killing the Messenger" Abstract *Trends plant Sci* 4(11): 452-457 (1999).

Wawrzynska et al. "Using a Suppression Subtractive Library-Based Approach to Identify Tobacco Genes Regulated in Response to Short-Term Sulphur Deficit" *Journal of Experimental Botany* 56(416): 1575-1590 (2005).

Wenke et al. "A Study of Betel Quid Carcinogenesis. II. Formation of *N*-Nitrosamines During Betel Quid Chewing" N-*Nitroso Compounds: Occurrence, Biological Effects and Relevance to Human Cancer* World Health Organization International Agency for Research on Cancer, IARC Scientific Publications No. 57, pp. 859-866 (1984).

Wiernik et al. "Effect of Air-Curing on the Chemical Composition of Tobacco" *Svenska Tobaks AB, Department Reserca, Recent Advances in Tobacco Science* 21:39-80 (1995).

Winz et al. "Molecular Interactions Between the Specialist Herbivore *Manduca sexta* (Lepidoptera, Sphingidae) and its Natural Host *Nicotiana attenuata*. IV. Insect-Induced Ethylene Reduces jasmonate-Induced Nicotine Accumulation by Regulating Putrescine *N*-Methyltransferase Transcripts" *Plant Physiology* 125: 2189-2202 (2001).

Wolbang et al. "Auxin Promotes Gibberellin Biosynthesis in Decapitated Tobacco Plants" *Planta* 214: 153-157 (2001).

Zaridze et al. "The Effect of Nass Use and Smoking on the Risk of Oral Leukoplakia" *Cancer Detection and Prevention* 9: 435-440 (1986).

Abeyama et al. "A role for NF-κB-Dependent Gene Transactivation in Sunburn" *The Journal of Clinical Investigation* 105(12):1751-1759 (2000).

Adam et al. "Transcription of tobacco phytochrome-A genes initiates at multiple start sites and requires multiple *cis*-acting regulatory elements" *Plant Mol. Biol.* 29(5):983-993 (1995).

Akimoto et al. "Growth Inhibition of Cultured Human Tenon's Fibroblastic Cells by Targeting the E2F Transcription Factor" *Exp. Eye Res.* 67:395-401 (1998).

Aparicio et al. "Recognition of *cis*-acting sequences in RNA 3 of *Prunus necrotic ringspot virus* by the replicase of *Alfalfa mosaic virus*" *J. Gen. Virol.* 82(Pt 4):947-951 (2001).

Beck et al. "Nucleotide Sequence and Exact Localization of the Neomycin Phosphotransferase Gene from Transposon Tn 5" *Gene* 19:327-336 (1982).

Bevan & Flavell, "A Chimaeric Antibiotic Resistance Gene as a Selectable Marker for Plant Cell Transformation" *Nature* 304:184-187 (1983).

Blastn 2.2.3 RID: 1028939485-09139-26659 http://www.ncbi.nlm.nih.gov/blast/Blast.cgi.

Blastn 2.2.3 RID: 1029876573-03236-18654 http://www.ncbi.nlm.nih.gov/blast/Blast.cgi.

Bogusz et al. "Functioning haemoglobin Genes in Non-Nodulating Plants" *Nature* 331:178-180 (1988).

Borisjuk et al. "Tobacco ribosomal DNA spacer element stimulates amplification and expression of heterologous genes" *Nat. Biotechnol.* 18(12):1303-1306 (2000).

Burtin, D., et al. Overexpression of Arginine Decarboxylase in Transgenic Plants *Biochem. J.* 325 (Part 2):331-337 (1997).

Bush, et al. "Nicotine Biosynthetic Enzymes of Burley Tobacco" *Tobacco Abstracts*, 24:260 (1980).

Bush, et al. "Physiological Aspects of Genetic Variation in Nicotine Content in Tobacco (*Nicotiana tabacum*)" *Tobacco Abstracst* 23:380 (1979).

Bustos et al. "Regulation of β-glucuronidase expression in transgenic tobacco plants by an A/T-rich, cis-acting sequence found upstream of a French bean β-phaseolin gene" *Plant Cell* 1(9):839-853.

Chilton et al. "Tailoring the Agrobacterium Ti Plasmid as a Vector for Plant Genetic Engineering" *Stadler Symp.* 13: 39-53 (1981).

Clusel et al. "Inhibition of HSV-1 proliferation by decoy phosphodiester oligonucleotides containing ICP4 recognition sequences" *Gene Expr.* 4(6):301-309 (1995).

Colbere-Garapin et al. "A New Dominant Hybrid Selective Marker for Higher Eukaryotic Cells" *J. Mol. Biol.* 150:1-14 (1981).

Conkling, et al. "Isolation of transcriptionally regulated root-specific genes from tobacco" *Plant Physiology*, 93( 3):1203-1211 (1990).

International Search Report to PCT/US98/11893—date of mailing Oct. 22, 1998.

Cornelissen, et al. "Both RNA Level and Translation Efficiency are Reduced by Anti-Sense RNA in Transgenic Tobacco" *Nucleic Acids Res.* 17(3): 833-843 (1989).

Crowley, et al., "Phenocopy of Discoidin 1-Minus Mutants by Antisense Transformation" *Cell* 43 (Part 2):633-641 (1985).

Cuozzo, et al. "Viral Protection in Transgenic Tobacco Plants Expressing the Cucumber Mosaic Virus Coat Protein Or Its Antisense RNA" *Biotechnology* 6:549-557 (1988).

D'Acquisto et al. "Local Administration of Transcription Factor Decoy Oligonucleotides to Nuclear Factor-κB Prevents Carrageenin-Induced Inflammation in Rat Hind Paw" *Gene Therapy* 7:1731-1737 (2000).

Database EMBL Online! EB1; clone TAP0198, Mar. 5, 1996, XP002285509, 2 pages.

Database entry of Ensembl Human Genome Server, AC006461.2.1.181215, BLASTN 2.0a13MP-WashU [Jun. 10, 1997], 2 pp.

Database entry of Ensembl Human Genome Server, AC024028.10.1.176278, BLASTN 2.0a13MP-WashU [Jun. 10, 1997], 3 pp.

Database entry of Ensembl Human Genome Server, AC069205.6.1.132242, BLASTN 2.0a13MP-WashU [Jun. 10, 1997], 1 pp.

Database entry of Ensembl Human Genome Server, AC097498.3.1.144511, BLASTN 2.0a13MP-WashU [Jun. 10, 1997], 1 pp.

Database entry of Ensembl Human Genome Server, AC104785.4. 111369.213599, BLASTN 2.0a13MP-WashU [Jun. 10, 1997], 1 pp.
Database entry of Ensembl Human Genome Server, AC105416.3. 1.123331, BLASTN 2.0a13MP-WashU [Jun. 10, 1997], 1 pp.
Database entry of Ensembl Human Genome Server, AC108146.3. 1.91810, BLASTN 2.0a13MP-WashU [Jun. 10, 1997], 1 pp (AC108146.3.1.91810?).
Database entry of Ensembl Human Genome Server, AC115109.2. 1.59356, BLASTN 2.0a13MP-WashU [Jun. 10, 1997], 1 pp.
Database GENSEQ Online! Sep. 8, 1994, retrieved from EBI, accession No. NTU08931, Database accession No. U08931.
Davies and Jimenez "A New Selective Agent for Eukaryotic Cloning Vectors" *Am. J. Trop. Med. Hyg.* 29(5)Supp:1089-1092 (1980).
Delauney, et al. "A Stable Bifunctional Antisense Transcript Inhibiting Gene Expression in Transgenic Plants" *Proc. Natl. Acad. Sci. USA* 85:4300-4304 (1988).
Depicker et al. "Nopaline Sythase: Transcript Mapping and DNA Sequence" *Journal of Molecular and Applied Genetics* 1(6):561-573 (1982).
Ecker, et al. "Inhibition of Gene Expression in Plant Cells by Expression of Antisense RNA" *Proc. Natl. Acad. Sci. USA* 83:5372-5376 (1986).
Ehsan et al. "Long-term stabilization of vein graft wall architecture and prolonged resistance to experimental atherosclerosis after E2F decoy oligonucleotide gene therapy" *J. Thorac. Cardiovasc. Surg.* 121(4):714-722 (2001).
European Search Report Application No. 04004191.5, Jul. 12, 2004.
European Search Report Application No. 04004192.3, Jul. 12, 2004.
Evans et al. Distribution of Root in mRNA Species in Other Vegetative Organs of Pea (*Pisum sativum* L.) *Mol. Gen. Genet.* 214:153-157 (1988).
Feth, et al. "Regulation in Tobacco Callus or Enzyme Activities of the Nicotine Pathway" *Planta*, 168: 402-407 (1986).
Fobert et al. "T-DNA Tagging of a Seed Coat-Specific Cryptic Promoter in Tobacco" *Plant Journal* 6(4):567-577 (1994).
Fraley et al. "Expression of Bacterial Genes in Plant Cells" *Proc. Natl. Acad. Sci. USA* 80:4803-4807 (1983).
Fraley et al. "Use of Chimeric Gene to Confer Antibiotic Resistance to Plant Cells" *Advances in Gene Technology: Molecular Genetics of Plants and Animals* 20:211-221 (1983).
Framond et al. "Mini-Ti: A New Vector Strategy for Plant Genetic Engineering" *BIO/TECHNOLOGY* 5:262-269 (1983).
Fuller et al. "Soybean Nodulin Genes: Analysis of cDNA Clones Reveals Several Major Tissue-Specific Sequences in Nitrogen-Fixing Root Nodules" *Proc. Natl. Acad. Sci USA* 80:2594-2598 (1983).
Geffers et al. "Anaerobiosis-specific interaction of tobacco nuclear factors with *cis*-regulatory sequences in the maize *GapC4* promoter" *Plant Mol. Biol.* 43(1):11-21 (2000).
Genbank entry AB005879. *Nicotania tabacum* mRNA for BYJ6, Feb. 5, 1999, 2 pp.
Genbank entry AC002131. *Arabidopsis thaliana* chromosome 1 BAC F12F1 sequence, May 28, 1998, 38 pp.
Genbank entry AC006461. *Homo sapiens* BAC clone RP11-343N14 from 2, Mar. 1, 2002, 65 pp.
Genbank entry AC021028. *Homo sapiens* clone RP11-137H2 from 10, 44 pp.
Genbank entry AC024028. *Homo sapiens* BAC clone RP11-151M24 from 7, Nov. 7, 2001, 68 pp.
Genbank entry AC069205. *Homo sapiens* BAC clone RP11-735P12 from 2, Jan. 9, 2002, 46 pp.
Genbank entry AC079141. *Homo sapiens* BAC clone RP11-502A23 from 4, Nov. 7, 2001, 43 pp.
Genbank entry AC097498. *Homo sapiens* BAC clone RP11-326N15 from 4, Mar. 1, 2002, 51 pp.
Genbank entry AC105416. *Homo sapiens* BAC clone RP11-3108A13 from 4, Jun. 12, 2002, 47 pp.
Genbank entry AC108146. *Homo sapiens* BAC clone RP11-437H3 from 2, Mar. 9, 2002, 32 pp.
Genbank entry AC115109. *Homo sapiens* BAC clone RP11-78I10 from 2, May 29, 2002, 23 pp.
Genbank entry AR164048. Sequence 7 from patent US 6271031, Oct. 17, 2001, 1 pp.
Genbank entry AR164050. Sequence 11 from patent US 6271031, Oct. 17, 2001, 1 pp.
Genbank entry AX344860. Sequence 285 from patent US WO0200927, Feb. 1, 2002, 4 pp.
Genbank entry PBU27809. Peanut bud necrosis virus S segment non-structural protein and nucleocapsid protein genes, Jul. 23, 1996, 3 pp.
Halk et al. "Cloning of Alfalfa Mosaic Virus Coat Protein Gene and Anti-Sense RNA into Binary Vector and Their Expression in Transformed Tobacco Tissue" *Molecular Strategies for Crop Protection* p. 41 (2004) (Abstract).
Hemenway, et al. "Analysis of the Mechanism of Protection in Transgenic Plants Expressing the Potato Virus × Coat Protein or Its Antisense RNA" *EMBO J.* 7(5):1273-1280 (1988).
Hermaisteens et al. "The *Agrobacterium tumefaciens* Ti Plasmid as a Host Vector System for Introducing Foreign DNA in Plant Cells" *Nature* 287:654-656 (1980).
Herrera-Estrella et al. "Chimeric Genes as Dominant Selectable Markers in Plant Cells" *The EMBO Journal* 2(6):987-995 (1993).
Herrera-Estrella et al. "Expression of Chimaeric Genes Transferred into Plant Cells Using a Ti-Plasmid-Derived Vector" *Nature* 303:209-213 (1983).
Holmberg, et al. "Transgenic tobacco expressing *Vitreoscilla* hemoglobin exhibits enhanced growth altered metabolite production" *Nature Biotechnology* 15:244-247 (1997).
Hookykaas et al. "The Ti-Plasmid of Agrobacterium Tumefaciens: A Natural Genetic Engineer" *TIBS* 307-309 (1985).
Horsch et al. "A Simple and General Method for Transferring Genes into Plants" *Science* 227:1229-1231 (1985).
Hsu et al. "Phloem Mobility of Xenobiotics VL a Phloem-Mobile Pro-Nematocide based on Oxamyl Exhibiting Root-Specific Activation in Transgenic Tobacco" *Pestic. Sci.* 44:9-19 (1995).
Hughes, Kelly T. et al., The *Salmonella typhimurium nad*C Gene: Sequence Determination by Use of Mud-P22 and Purification of Quinolinate Phosphoribosyltransferase, *Journal of Bacteriology* 175(2): 479-486 (Jan. 1993).
Imanishi et al. "Differential Induction by Methyl Jasmonate of Genes Encoding Ornithine Decarboxylase and Other Enzymes Involved in Nicotine Biosynthesis in Tobacco Cell Cultures" *Plant Molecular Biology* 38:1101-1111 (1998).
International Search Report for International Application Serial No. PCT/US01/26788 dated Jul. 17, 2002.
Izant, et al. "Constitutive and conditional Suppression of Exogenous Genes by Anti-Sense RNA" *Science* 229: 345-352 (1985).
Izant, et al. "Inhibition of Thymidine Kinase Gene Expression by Anti-Sense RNA: A Molecular Approach to Genetic Analysis" *Cell* 36: 1007-1015 (1984).
Johnson et al. "Regulation of DNA binding and *trans*-activation by a xenobiotic stress-activated plant transcription factor" *J. Biol. Chem.* 276(1):172-178 (2001).
Keller et al. "Specific Expression of Novel Cell Wall Hydroxyproline-Rich Glycoprotein Gene in Lateral Root Initiation" *Genes & Dev.* 3:1639-1646 (1989).
Kim, et al., "Stable Reduction of Thymidine Kinase Activity in Cells Expressing High Levels of Anti-Sense RNA" *Cell* 42:129-138 (1985).
Kitamoto et al. "Increased Activity of Nuclear Factor- κB Participates in Cardiovascular Remodeling Induced by Chronic Inhibition of Nitric Oxide Synthesis in Rats" *Circulation* 102:806-812 (2000).
Konopka "Rev-binding aptamer and CMV promoter act as decoys to inhibit HIVreplication" *Gene* 255(2):235-244 (2000).
Kubota, et al. "Cloning of a Nuclear-Encoded Photosystem 1 Gene, *psaEB*, in *Nicotiana sylvestris*" *Plant Physiol* 108:1297-1298 (1995).
Lam, et al. "Site-Specific Mutations Alter In Vitro Factor Binding and Change Promoter Expression Pattern in Transgenic Plants" *Proc. Nat. Acad. Sci. USA* 86:7890-7894 (1989).
Lerner et al. "Cloning and Characterization of Root-Specific Barley Lectin" *Plant Physiology* 91:124-129 (1989).
Lichtenstein "Anti-sense RNA As A Tool To Study Plant Gene Expression" *Nature* 333: 801-802 (1988).

Lorz et al. "Transformation Studies Using Synthetic DNA Vectors Coding For Antibiotic Resistance" *Plant Tissue Culture* 511-512 (1982).

Maniatis et al. "Regulation of Inducible and Tissue Specific Gene Expression" *Science* 237:1237-1244 (1987).

Mann et al. "Pressure-Mediated Oligonucleotide Transfection of Rat and Human Cardiovascular Tissues" *Proc. Natl. Acad. Sci. USA* 96:6411-6416 (1999).

McGarry, et al. "Inhibition of Heat Shock Protein Synthesis by Heat-Inducible Antisense RNA" *Proc. Natl. Acad. Sci. USA* 83:399-403 (1986).

Melton "Injected Anti-Sense RNAs Specifically Block Messenger RNA Translation In Vivo" *Proc. Natl. Acad. Sci. USA*, 82:144-148 (1985).

Mischiati et al. "Interaction of the Human NF-κB p52 Transcription Factor with DNA-PNA Hybrids Mimicking the NF-κB Binding Sites of the Human Immunodeficiency Virus Type 1 Promoter" *The Journal of Biological Chemistry* 274(46):33114-33122 (1999).

Mizuno, et al. "A Unique Mechanism Regulating Gene Expression: Translational Inhibition By a Complementary RNA Transcript (micRNA)" *Proc. Natl. Acad. Sci. USA* 81:1966-1970 (1984).

Morishita et al. "A gene therapy strategy using a transcription factor decoy of the E2F binding site inhibits smooth muscle proliferation in vivo" *Proc. Natl. Acad. Sci. USA* 92(13):5855-5859 (1995).

Morishita, et al. "Application of Transcription Factor "Decoy" Strategy as Means of Gene Therapy and Study of Gene Expression in Cardiovascular Disease" *Circ. Res.* 82:1023-1028 (1998).

Nastruzzi et al. "Liposomes as Carriers for DNA-PNA Hybrids" *Journal of Controlled Release* 68:237-249 (2000).

NCBI Sequence Viewer Accession No. D42070 Tobacco psaEb Locus: TOBPSAEB Jan. 10, 2003.

NCBI Sequence Viewer Accession No. X70902 *N.tobacum* T85 Locus: NTT85A Apr. 18, 2005.

Ohta, et al, "Metabolic Key Step Discriminating Nicotine Producing Tobacco Callus Strain From Ineffective One" *Biochem. Physiol. Pflanzen*, 175:382-385 (1980).

Park et al., "Dual Blockade of Cyclic AMP Response Element-(CRE) and Ap-1-Directed Transcription by CRE-Transcription Factor Decoy Oligonucleotide" *The Journal of Biological Chemistry* 274(3):1573-1580 (1990).

Pestka, et al. "Anti-mRNA: Specific Inhibition of Translation of Single mRNA Molecules" *Proc. Natl. Acad. Sci. USA*, 81:7525-7528 (1984).

Poulsen et al. "Dissection of 5' Upstream Sequences for Selective Expression of the *Nicotiana plumbaginifolia* rbcS-8B gene" *Mol. Gen. Genet.* 214:16-23 (1988).

Preiss, et al. "Molecular genetics of Krüppel, A Gene Required for Segmentation of the *Drosphila* Embryo" *Nature* 313:27-32 (1985).

Rafty et al. "Novel Negative Regulator Element in the Platelet-Derived Growth Factor B Chain Promoter That Mediates ERK-Dependent Transcriptional Repression" *The Journal of Biological Chemistry*, 275(15):11478-11483 (2000).

Results of search of Genbank Database, BLASTN 2.2.3 [Apr. 24, 2002], RID:1026175671-06698-1397, 15pp.

Results of search of Genbank Database, BLASTN 2.2.3 [Apr. 24, 2002], RID:1026319792-012476-25945, 30 pp.

Rezaian, et al. "Anti-Sense RNAs of Cucumber Mosaic Virus in Transgenic Plants Assessed For Control of the Virus" *Plant Molecular Biology* 11: 463-471 (1988).

Rodermel, et al. "Nuclear-Organelle Interactions: Nuclear Antisense Gene Inhibits Ribulose Biphosphate Carboxylase Enzyme Levels In Transformed Tobacco Plants" *Cell* 55: 673-681 (1988).

Rosenberg, et al. "Production of Phenocopies by *Krüppel* Antisense RNA Injection Into *Drosphila* Embryos" *Nature* 313,:703-706 (1985).

Rothstein, et al. "Stable and Heritable Inhibition of the Expression of Nopaline Synthase in Tobacco Expressing Antisense RNA" *Proc. Natl. Sci. USA* 84:8439-8443 (1987).

Sandler, et al. "Inhibition of Gene Expression in Transformed Plants by Antisense RNA" *Plant Molecular Biology* 11:301-310 (1988).

Sanford et al. "The Biolistic Process" *Trends in Biotechnology* 6:299-302 (1988).

Sayanarayana et al. "Peanut Bud Necrosis Tospovirus S RNA: Complete Nucleotide Sequence, Genome Organization and Homology to Other Tospoviruses" *Arch. Virol.* 141(1):85-98 (1996).

Saunders, et al. "Comparison of Nicotine Biosynthetic Enzymes in Nicotine Level Genotypes of Burley Tobacco" American Society of Agronomy, 90th Annual Meeting, p. 84, Chicago IL, Dec. 2-8, 1978.

Saunders, et al. "Enzyme Activities in Nicotine Biosynthesis in *Nicotiana tabacum*" *Journal of National Products*, 41 p. 646 (1978) (Abstract).

Sharma et al. "Transcription factor decoy approach to decipher the role of NF-κB in oncogenesis" *Anticancer Res.* 16(1):61-70 (1996).

Sheehey, et al. "Reduction of Polygalacturonase Activity in Tomato Fruit by Antisense RNA" *Proc. Natl. Acad. Sci. USA*, 85:8805-8809 (1988).

Siebertz et al. "*cis*-Analysis of the wound-inducible promoter *wun1* in transgenic tobacco plants and histochemical localization of its expression" *Plant Cell* 1(10):961-968 (1989).

Singer et al. Transcription: The Transfer of DNA Sequence Information to RNA, In *Genes and Genomes*, section 3.2: 134-145, University Science Books, Mill Valley, CA (1991).

Song, Wen, *Molecular characterizations of two tobacco root-specific genes: TobRB7 and NtQPT1*(1997); UMI, Accession No. A DG9804246, Diss. Abstr. Int., B, 58( 8),:4061.

Takata, et al. "Novel *Cis* Element for Tissue-Specific Transcription of Rat Platelet-Derived Growth Factor β-Receptor Gene" *Hypertension* 33(II):298-302 (1999).

The Sanger Centre, "Toward a Complete Human Genome Sequence" Cold Spring Harbor Laboratory Press 1097-1108 (1988).

Theologis et al. "Sequence and Analysis of Chromosome 1 of the Plant *Arabidopsis thaliana*" *Nature*, 408: 816-820 (2000).

Travers "Regulation by Anti-Sense RNA" *Nature*, 311:410 (1984).

Van der Krol, et al. "An Anti-Sense Chalcone Synthase Gene in Transgenic Plants Inhibits Flower Pigmentation" *Nature*, 333: 866-869 (1988).

Van der Krol, et al. "Antisense Genes in Plants; An Overview" *Gene* 72: 45-50 (1988).

Van der Krol, et al. "Modulation of Eukaryotic Gene Expression by Complementary RNA or DNA Sequences" *Biotechniques* 6:958-976 (1988).

Wadgaonkar et al. "CREB-binding protein is a nuclear integrator of nuclear factor-κB and p53 signaling." *J. Biol. Chem.* 274(4):1879-1882 (1999).

Wagner, et al. "Regulation in Tobacco Callus of Enzyme Activities of the Nicotine Pathway" *Planta* 168: 408-413.

Wagner, et al. "The Regulation of Enzyme Activities of the Nicotine Pathway in Tobacco" *Physiol. Plantarum*, 68:667-672 (1986).

Wagner, Roland, et al. "Determination of Quinolinic Acid Phosphoribosyl-Transferase in Tobacco" *Phytochemistry* 23( 9):1881-1883 (1984).

Wang et al. "Characterization of *cis*-acting elements regulating transcription from the promoter of a constitutively active rice actin gene" *Mol. Cell Biol.* 12(8):3399-3406 (1992).

Wang et al. "Right 25 bp Terminus Sequence of the Nopaline T-DNA is Essential for and Determines Direction of DNA Transfer from Agrobacterium to the Plant Genome" *Cell* 38:455-462 (1984).

Wang, et al. "Targeted Disruption of Stat6 DNA Binding Activity by an Oligonucleotide Decoy Blocks IL-4-Driven $T_H2$ Cell Response" *Blood* 95(4): 1249-1257 (2000).

Watanabe et al. "Cloning and Expression of Two Genes Encoding Auxin-Binding Proteins From Tobacco" *Plant Molecular Biology* 36:63-74 (1998).

Weintraub, et al. "Anti-sense RNA as a Molecular Tool for Genetic Analysis" *Trends in Genetics*, 1:22-25 (1985).

West et al. "Duplex-Duplex Interactions Catalyzed by RecA Protein Allow Strand Exchanges to Pass Double-Strand Breaks in DNA" *Cell* 683-691 (1984).

Yamamoto "A Tobacco Root-Specific Gene: Characterization and Regulation of its Expression" *J. Cell Biochem.* 13(D) (Suppl.) (1989).

Yamamoto "A Tobacco-Specific Gene; Characterization and Regulation of its Transcription" Ph.D. Thesis submitted to the Graduate Faculty of North Carolina State University Genetics Department (1989).

Yamamoto et al. "Root-Specific Genes from Tobacco and *Arabidopsis* homologous to Evolutionary Conserved Gene Family of Membrane Channel Proteins" *Nucleic Acids Research* 18:7449 (1990).

Yamamoto et al. "Characterization of *cis*-acting sequences regulating root-specific gene expression in tobacco" *Plant Cell* 3(4):371-382 (1991).

Hashimoto et al. "Intraspecific Variability of the Tandem Repeats in *Nicotiana* Putrescine *N*-Methyltransferase", *Plant Molecular Biology*. 37:25-37 (1998).

International Search Report corresponding to PCT/US01/47371 mailed on Aug. 18, 2003.

Riechers et al. "Structure and Expression of the Gene Family Encoding Putrescine *N*-Methyltransferase in *Nicotiana tabacum*: New Clues to the Evolutionary Origin of Cultivated Tobacco" *Plant Molecular Biology* 41:387-401 (1999).

* cited by examiner

SEQUENCE LISTING

<160> NUMBER OF SEQ ID NOS: 11

<210> SEQ ID NO 1
<211> LENGTH: 742
<212> TYPE: DNA
<213> ORGANISM: NtPMT promoter

<400> SEQUENCE: 1

```
gtataccaaa aatcaattca accccaaaa cataatacaa ccaatgttaa tgcaatatct    60
ctgctgctat cacgaagata attgtagctc acgaaagtag gatacattat gtaggttaca   120
tcacatagag gtaatctaaa gctcccaata ataagatgtg taatgttgat tatgtagaaa   180
tttgccaggt tatttagaat aaacaagaag aggagaaaaa agtacaatt tacctgaact    240
cttgaatgta tcctacaaat aacctagact tcatggacgt cagttgtcag tttacttttg   300
ttttaatggt acatcatttg tcaaatactt tatttggata aaaacagttt tgcctaagga   360
gtaaacagat ccggagtaag aaagcagacg attaaagcaa tttttaaaaa aggagagaga   420
aattaatgag cacacacata tactagtgaa attagggtac taatttacta ataattgcac   480
cgagacaaac ttatatttta gttccaaaat gtcagtctaa ccctgcacgt tgtaataaat   540
ttttaactct attatattat atcgagttgc gccctccact cctcggtgtc caaattgtat   600
ttaaatgcat agatgtttaa tgggagtgta cagcaagctt tcggaaaata caaaccataa   660
tactttctct tcttcaattt gtttagttta attttgaaaa tggaagtcat atctaccaac   720
acaaatggct ctaccatctt ca                                            742
```

<210> SEQ ID NO 2
<211> LENGTH: 732
<212> TYPE: DNA
<213> ORGANISM: Deletion mutant of PMT promoter

<400> SEQUENCE: 2

```
aatcaattca accccaaaa cataatacaa ccaatgttaa tgcaatatct ctgctgctat     60
cacgaagata attgtagctc acgaaagtag gatacattat gtaggttaca tcacatagag   120
gtaatctaaa gctcccaata ataagatgtg taatgttgat tatgtagaaa tttgccaggt   180
tatttagaat aaacaagaag aggagaaaaa agtacaatt tacctgaact cttgaatgta    240
tcctacaaat aacctagact tcatggacgt cagttgtcag tttacttttg ttttaatggt   300
acatcatttg tcaaatactt tatttggata aaaacagttt tgcctaagga gtaaacagat   360
ccggagtaag aaagcagacg attaaagcaa tttttaaaaa aggagagaga aattaatgag   420
cacacacata tactagtgaa attagggtac taatttacta ataattgcac cgagacaaac   480
ttatatttta gttccaaaat gtcagtctaa ccctgcacgt tgtaataaat ttttaactct   540
attatattat atcgagttgc gccctccact cctcggtgtc caaattgtat ttaaatgcat   600
agatgtttaa tgggagtgta cagcaagctt tcggaaaata caaaccataa tactttctct   660
tcttcaattt gtttagttta attttgaaaa tggaagtcat atctaccaac acaaatggct   720
ctaccatctt ca                                                       732
```

<210> SEQ ID NO 3
<211> LENGTH: 722
<212> TYPE: DNA
<213> ORGANISM: Deletion mutant of PMT promoter

<400> SEQUENCE: 3

```
acccccaaaa cataatacaa ccaatgttaa tgcaatatct ctgctgctat cacgaagata      60
attgtagctc acgaaagtag gatacattat gtaggttaca tcacatagag gtaatctaaa    120
gctcccaata ataagatgtg taatgttgat tatgtagaaa tttgccaggt tatttagaat    180
aaacaagaag aggagaaaaa aagtacaatt tacctgaact cttgaatgta tcctacaaat    240
aacctagact tcatggacgt cagttgtcag tttacttttg ttttaatggt acatcatttg    300
tcaaatactt tatttggata aaaacagttt tgcctaagga gtaaacagat ccggagtaag    360
aaagcagacg attaaagcaa ttttaaaaa aggagagaga aattaatgag cacacacata    420
tactagtgaa attagggtac taatttacta ataattgcac cgagacaaac ttatattta    480 gttccaaaat gtcagtctaa ccctgcacgt tgtaataaat ttttaactct attatattat    540
atcgagttgc gccctccact cctcggtgtc caaattgtat ttaaatgcat agatgtttaa    600
tgggagtgta cagcaagctt tcggaaaata caaaccataa tactttctct tcttcaattt    660
gtttagttta attttgaaaa tggaagtcat atctaccaac acaaatggct ctaccatctt    720
ca                                                                  722

<210> SEQ ID NO 4
<211> LENGTH: 712
<212> TYPE: DNA
<213> ORGANISM: Deletion mutant of PMT promoter

<400> SEQUENCE: 4
cataatacaa ccaatgttaa tgcaatatct ctgctgctat cacgaagata attgtagctc     60
acgaaagtag gatacattat gtaggttaca tcacatagag gtaatctaaa gctcccaata    120
ataagatgtg taatgttgat tatgtagaaa tttgccaggt tatttagaat aaacaagaag    180
aggagaaaaa aagtacaatt tacctgaact cttgaatgta tcctacaaat aacctagact    240
tcatggacgt cagttgtcag tttacttttg ttttaatggt acatcatttg tcaaatactt    300
tatttggata aaaacagttt tgcctaagga gtaaacagat ccggagtaag aaagcagacg    360
attaaagcaa ttttaaaaa aggagagaga aattaatgag cacacacata tactagtgaa    420
attagggtac taatttacta ataattgcac cgagacaaac ttatattta gttccaaaat    480 gtcagtctaa ccctgcacgt tgtaataaat ttttaactct attatattat atcgagttgc    540
gccctccact cctcggtgtc caaattgtat ttaaatgcat agatgtttaa tgggagtgta    600
cagcaagctt tcggaaaata caaaccataa tactttctct tcttcaattt gtttagttta    660
attttgaaaa tggaagtcat atctaccaac acaaatggct ctaccatctt ca            712

<210> SEQ ID NO 5
<211> LENGTH: 702
<212> TYPE: DNA
<213> ORGANISM: Deletion mutant of PMT promoter

<400> SEQUENCE: 5
ccaatgttaa tgcaatatct ctgctgctat cacgaagata attgtagctc acgaaagtag     60
gatacattat gtaggttaca tcacatagag gtaatctaaa gctcccaata ataagatgtg    120
taatgttgat tatgtagaaa tttgccaggt tatttagaat aaacaagaag aggagaaaaa    180
aagtacaatt tacctgaact cttgaatgta tcctacaaat aacctagact tcatggacgt    240
cagttgtcag tttacttttg ttttaatggt acatcatttg tcaaatactt tatttggata    300
aaaacagttt tgcctaagga gtaaacagat ccggagtaag aaagcagacg attaaagcaa    360
```

-continued

```
ttttttaaaaa aggagagaga aattaatgag cacacacata tactagtgaa attagggtac      420
taatttacta ataattgcac cgagacaaac ttatatttta gttccaaaat gtcagtctaa      480
ccctgcacgt tgtaataaat ttttaactct attatattat atcgagttgc gccctccact      540
cctcggtgtc caaattgtat ttaaatgcat agatgtttaa tgggagtgta cagcaagctt      600
tcggaaaata caaccataa  actttctct tcttcaattt gtttagttta attttgaaaa       660
tggaagtcat atctaccaac acaaatggct ctaccatctt ca                        702
```

<210> SEQ ID NO 6
<211> LENGTH: 692
<212> TYPE: DNA
<213> ORGANISM: Deletion mutant of PMT promoter

<400> SEQUENCE: 6

```
tgcaatatct ctgctgctat cacgaagata attgtagctc acgaaagtag gatacattat      60
gtaggttaca tcacatagag gtaatctaaa gctcccaata ataagatgtg taatgttgat      120
tatgtagaaa tttgccaggt tatttagaat aaacaagaag aggagaaaaa aagtacaatt      180
tacctgaact cttgaatgta tcctacaaat aacctagact tcatggacgt cagttgtcag      240
tttacttttg ttttaatggt acatcatttg tcaaatactt tatttggata aaaacagttt      300
tgcctaagga gtaaacagat ccggagtaag aaagcagacg attaaagcaa ttttaaaaa      360 aggagagaga aattaatgag cacacacata tactagtgaa attagggtac taatttacta      420
ataattgcac cgagacaaac ttatatttta gttccaaaat gtcagtctaa ccctgcacgt      480
tgtaataaat ttttaactct attatattat atcgagttgc gccctccact cctcggtgtc      540
caaattgtat ttaaatgcat agatgtttaa tgggagtgta cagcaagctt tcggaaaata      600 caaccataa  actttctct tcttcaattt gtttagttta attttgaaaa tggaagtcat      660
atctaccaac acaaatggct ctaccatctt ca                                   692
```

<210> SEQ ID NO 7
<211> LENGTH: 642
<212> TYPE: DNA
<213> ORGANISM: Deletion mutant of PMT promoter

<400> SEQUENCE: 7

```
gtataccaaa aatcaattca accccaaaa cataatacaa ccaatgttaa tgcaatatct       60
ctgctgctat cacgaagata attgtagctc acgaaagtag gatacattat gtaggttaca     120
tcacatagag gtaatctaaa gctcccaata ataagatgtg taatgttgat tatgtagaaa     180
tttgccaggt tatttagaat aaacaagaag aggagaaaaa aagtacaatt tacctgaact     240
cttgaatgta tcctacaaat aacctagact tcatggacgt cagttgtcag tttacttttg     300
ttttaatggt acatcatttg tcaaatactt tatttggata aaaacagttt tgcctaagga     360
gtaaacagat ccggagtaag aaagcagacg attaaagcaa ttttaaaaa aggagagaga     420 aattaatgag cacacacata tactagtgaa attagggtac taatttacta ataattgcac     480
cgagacaaac ttatatttta gttccaaaat gtcagtctaa ccctgcacgt tgtaataaat     540
ttttaactct attatattat atcgagttgc gccctccact cctcggtgtc caaattgtat     600
ttaaatgcat agatgtttaa tgggagtgta cagcaagctt tc                        642
```

<210> SEQ ID NO 8
<211> LENGTH: 630
<212> TYPE: DNA
<213> ORGANISM: Deletion mutant of PMT promoter

```
<400> SEQUENCE: 8
gtataccaaa aatcaattca accccaaaa cataatacaa ccaatgttaa tgcaatatct      60
ctgctgctat cacgaagata attgtagctc acgaaagtag gatacattat gtaggttaca    120
tcacatagag gtaatctaaa gctcccaata ataagatgtg taatgttgat tatgtagaaa    180
tttgccaggt tatttagaat aaacaagaag aggagaaaaa aagtacaatt tacctgaact    240
cttgaatgta tcctacaaat aacctagact tcatggacgt cagttgtcag tttacttttg    300
ttttaatggt acatcatttg tcaaatactt tatttggata aaaacagttt tgcctaagga    360
gtaaacagat ccggagtaag aaagcagacg attaaagcaa ttttttaaaaa aggagagaga   420 aattaatgag cacacacata tactagtgaa attagggtac taatttacta ataattgcac    480
cgagacaaac ttatatttta gttccaaaat gtcagtctaa ccctgcacgt tgtaataaat    540
ttttaactct attatattat atcgagttgc gccctccact cctcggtgtc caaattgtat    600
ttaaatgcat agatgtttaa tgggagtgta                                     630

<210> SEQ ID NO 9
<211> LENGTH: 620
<212> TYPE: DNA
<213> ORGANISM: Deletion mutant of PMT promoter

<400> SEQUENCE: 9
gtataccaaa aatcaattca accccaaaa cataatacaa ccaatgttaa tgcaatatct      60
ctgctgctat cacgaagata attgtagctc acgaaagtag gatacattat gtaggttaca    120
tcacatagag gtaatctaaa gctcccaata ataagatgtg taatgttgat tatgtagaaa    180
tttgccaggt tatttagaat aaacaagaag aggagaaaaa aagtacaatt tacctgaact    240
cttgaatgta tcctacaaat aacctagact tcatggacgt cagttgtcag tttacttttg    300
ttttaatggt acatcatttg tcaaatactt tatttggata aaaacagttt tgcctaagga    360
gtaaacagat ccggagtaag aaagcagacg attaaagcaa ttttttaaaaa aggagagaga   420 aattaatgag cacacacata tactagtgaa attagggtac taatttacta ataattgcac    480
cgagacaaac ttatatttta gttccaaaat gtcagtctaa ccctgcacgt tgtaataaat    540
ttttaactct attatattat atcgagttgc gccctccact cctcggtgtc caaattgtat    600
ttaaatgcat agatgtttaa                                                620

<210> SEQ ID NO 10
<211> LENGTH: 630
<212> TYPE: DNA
<213> ORGANISM: Deletion mutant of PMT promoter

<400> SEQUENCE: 10
aatcaattca accccaaaa cataatacaa ccaatgttaa tgcaatatct ctgctgctat      60
cacgaagata attgtagctc acgaaagtag gatacattat gtaggttaca tcacatagag   120
gtaatctaaa gctcccaata ataagatgtg taatgttgat tatgtagaaa tttgccaggt   180
tatttagaat aaacaagaag aggagaaaaa aagtacaatt tacctgaact cttgaatgta   240
tcctacaaat aacctagact tcatggacgt cagttgtcag tttacttttg ttttaatggt   300
acatcatttg tcaaatactt tatttggata aaaacagttt tgcctaagga gtaaacagat   360
ccggagtaag aaagcagacg attaaagcaa ttttttaaaaa aggagagaga aattaatgag   420
cacacacata tactagtgaa attagggtac taatttacta ataattgcac cgagacaaac   480
```

```
-continued ttatatttta gttccaaaat gtcagtctaa ccctgcacgt tgtaataaat ttttaactct      540
attatattat atcgagttgc gccctccact cctcggtgtc caaattgtat ttaaatgcat      600
agatgtttaa tgggagtgta cagcaagctt                                      630

<210> SEQ ID NO 11
<211> LENGTH: 610
<212> TYPE: DNA
<213> ORGANISM: Deletion mutant of PMT promoter

<400> SEQUENCE: 11 accccccaaaa cataatacaa ccaatgttaa tgcaatatct ctgctgctat cacgaagata      60
attgtagctc acgaaagtag gatacattat gtaggttaca tcacatagag gtaatctaaa     120
gctcccaata ataagatgtg taatgttgat tatgtagaaa tttgccaggt tatttagaat     180
aaacaagaag aggagaaaaa aagtacaatt tacctgaact cttgaatgta tcctacaaat     240
aacctagact tcatggacgt cagttgtcag tttacttttg ttttaatggt acatcatttg     300
tcaaatactt tatttggata aaaacagttt tgcctaagga gtaaacagat ccggagtaag     360
aaagcagacg attaaagcaa tttttaaaaa aggagagaga aattaatgag cacacacata     420
tactagtgaa attagggtac taatttacta ataattgcac cgagacaaac ttatatttta     480
gttccaaaat gtcagtctaa ccctgcacgt tgtaataaat ttttaactct attatattat     540
atcgagttgc gccctccact cctcggtgtc caaattgtat ttaaatgcat agatgtttaa     600
tgggagtgta                                                            610
```

PUTRESCINE-N-METHYLTRANSFERASE PROMOTER

CROSS-REFERENCE TO RELATED APPLICATIONS

This application is a 35 U.S.C. § 371 national phase application of PCT Application No. PCT/US01/47371, filed in English on Nov. 7, 2001, which claims the benefit of U.S. Provisional Application 60/246,448, filed on Nov. 7, 2000, the disclosures of which are incorporated by reference herein in their entireties.

FIELD OF THE INVENTION

The present invention concerns root-specific promoters useful in plants, along with methods of use thereof, constructs containing the same, and transgenic plants produced with such promoters.

BACKGROUND OF THE INVENTION

A promoter is generally defined as a nucleic acid sequence upsteam or downstream from a transcribed gene, and to which RNA polymerase must bind if it is to transcribe the flanking gene into messenger RNA. A promoter may consist of a number of different regulatory elements that affect a structural gene operationally associated with the promoter in different ways. For example, a regulatory element may enhance or repress expression of an associated structural gene, subject that gene to developmental regulation, or contribute to the tissue-specific regulation of that gene. Modifications to promoters can make possible optional patterns of gene expression, using recombinant DNA procedures. See, e.g., Old and Primrose, Principles of Gene Manipulation (4th Ed., 1989).

Transgenic plants expressing peptides that inhibit or kill a particular pest or pathogen provide a method for decreasing crop damage and loss. For example, expression of the *Bacillus thuringiensis* protein in transgenic corn provides resistance to the European corn borer. However, transgene expression in all tissues of a plant (constitutive expression) can be disadvantageous as it can expose non-target organisms to the transgenic protein and can increase the selective pressure for the development of pathogens and pests which are resistant to the transgenic protein. High levels of transgene expression throughout a plant may also negatively affect growth and yield of the plant. An alternative strategy is to express a toxic peptide only in the organ or tissue affected by a particular pest or pathogen. Implementation of this strategy against pests and pathogens that attack plant roots has been hampered by the lack of characterized root-specific promoters.

Transcription of a gene is initiated when a stable complex is formed between RNA polymerase enzyme and a gene promoter. Promoters generally occur at the beginning of all transcription units, are typically about 100 base pairs in length, and generally are located immediately upstream from the start site of transcription. See e.g., Maniatis et al., Science 236:1238 (1987). Promoters vary in their "strength"; that is, in their ability to accurately and efficiently initiate transcription. The RNA polymerase holoenzyme is thought to cover a region of about 50 bases immediately upstream of the transcribed region. In some cases the strength of transcription initiation may be enhanced by auxiliary proteins that bind adjacent to the region of the promoter which is immediately upstream from the transcribed DNA. See, e.g., Singer & Berg, Genes and Genomes, 140–145, University Science Books, Mill Valley, Cailf. (1991).

U.S. Pat. No. 5,459,252 to Conkling and Yamamoto describes the RB7 root promoter.

U.S. Pat. No. 5,837,876 to Conkling, Mendu and Song describes the RD2 root cortex specific promoter, also known as the NtQPT1 promoter.

SUMMARY OF THE INVENTION

A first aspect of the present invention is an isolated DNA molecule which directs root specific transcription of a downstream heterologous DNA segment in a plant cell. The promoter is a putrescine-N-methyltransferase (PMT) promoter, such as the tobacco PMT promoter or NtPMT1 promoter. Examples of promoters of the present invention include isolated DNA molecules having a sequence selected from the group consisting of (a) SEQ ID NOs:1–11 provided herein, and (b) DNA sequences which hybridize to any of SEQ ID NOS:1–11 or the complement thereof (preferably under stringent conditions), and which direct root specific transcription of a downstream heterologous DNA segment in a plant cell.

A further aspect of the present invention is an expression cassette comprising a tobacco PMT promoter and a heterologous DNA segment positioned downstream from, and operatively associated with, the promoter.

A further aspect of the present invention is an expression cassette comprising a root specific promoter and a heterologous DNA segment, the sequence of the root specific promoter as described herein Further aspects of the present invention are plant cells comprising the above described expression cassettes, methods of making transformed plants from such plant cells, and the transformed plants comprising such transformed plant cells.

DETAILED DESCRIPTION OF THE PREFERRED EMBODIMENTS

Figure 1:
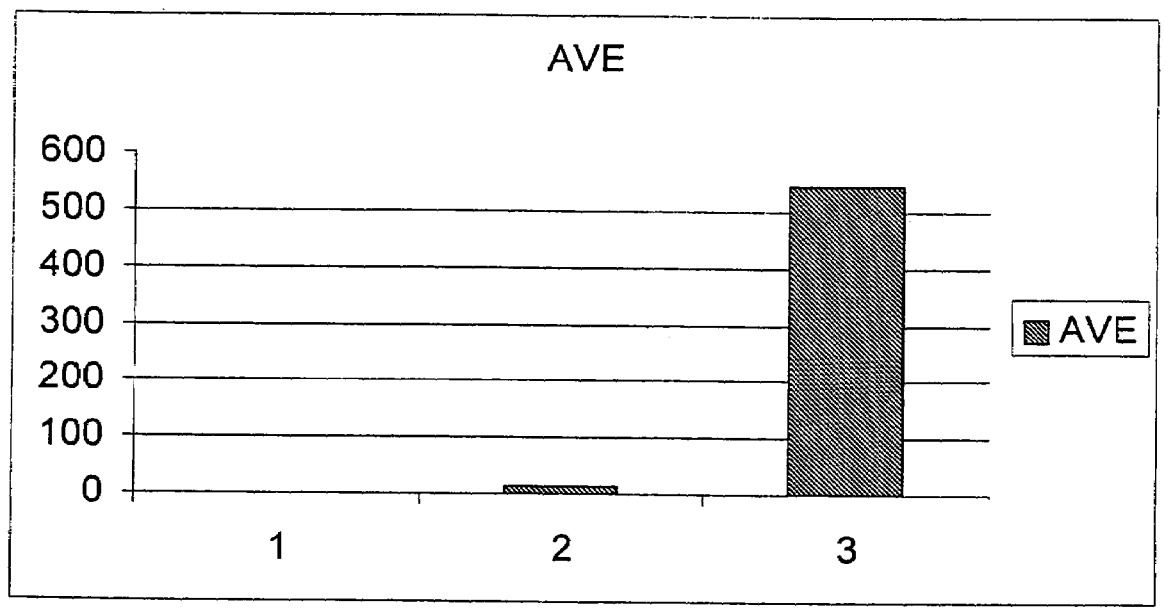
FIG. 1 shows average GUS expression levels in leaves (column 1), stems (column 2), and roots (column 3) directed by the PMT promoter.

Nucleotide sequences are presented herein by single strand only, in the 5' to 3' direction, from left to right. Nucleotides are represented herein in the manner recommended by the IUPAC-IUB Biochemical Nomenclature Commission.

Specific examples of root specific promoters of the present invention are DNA molecules which have a sequence corresponding to any one of those shown in SEQ ID NOS: 1–11, all of which are discussed in greater detail below. It will be apparent that other sequence fragments from the Tobacco PMT 5' flanking region, longer or shorter than the foregoing sequences, or with minor additions, deletions, or substitutions made thereto, can be prepared which will also carry the TobPMT root specific promoter, all of which are included within the present invention. A further aspect of the present invention includes promoters isolated from other tobacco genes, or from plants other than tobacco as set forth below, which are homologous to the tobacco PMT promoter and are capable of directing root specific transcription of a downstream heterologous DNA segment in a plant cell.

As used herein, a TobPMT promoter refers to a DNA molecule having a sequence identical to, or substantially homologous to, a continuous segment of the DNA found 5' to the transcribed region of the tobacco PMT gene. SEQ ID NO:1 given herein provides the sequence of the region found immediately 5' to the transcription start site in the TobPMT gene. TobPMT promoters include the at least 100 base pair region, the 150 base pair region, or preferably the 200 base pair region immediately 5' to the TobPMT transcribed region, and direct root specific expression. As used herein, regions that are "substantially homologous" are at least 75%, and more preferably are 80%, 85%, 90% or even 95% homologous to the nucleic acid sequence.

As used herein, a root specific promoter is a promoter that preferentially directs expression of an operatively associated DNA, nucleic acid or gene in root tissue, as compared to expression in leaf or stem tissue, or other tissues of the plant.

Root specific promoter sequences from other plants include those which are at least about 75 percent homologous (and more preferably 80%, 85%, 90% or even 95% homologous) to the approximately 100 base segment of the Tobacco PMT promoter immediately upstream of the transcribed DNA region, and which are capable of directing root specific transcription of a downstream heterologous DNA segment in a plant cell. Root specific promoters from other plants include those which are at least about 75 percent homologous (and more preferably 80%, 85%, 90% or even 95% homologous) to the continuous portions of the TobPMT promoter as defined herein by SEQ ID NOS: 1–11, and which are capable of directing root specific transcription of a downstream heterologous DNA segment in a plant cell. Percent homology may be determined by comparing the reference sequence, such as SEQ ID NO: 1 to 11, with another test sequence by the use of a suitable comparison algorithms or by visual inspection. In one embodiment, the substantial identity exists over a region of the sequences that is at least about 20 to 50 residues in length. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l . Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

High stringency hybridization conditions which will permit homologous DNA sequences to hybridize to a DNA sequence as given herein are well known in the art. For example, hybridization of such sequences to DNA disclosed herein may be carried out in 25% formamide, 5×SSC, 5×Denhardt's solution, with 100 ug/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° or even 70° C. using a standard in situ hybridization assay. (See Sambrook et al., Molecular Cloning, A Laboratory Manual (2d Ed. 1989)(Cold Spring Harbor Laboratory)). In general, plant DNA sequences which code for root specific promoters and which hybridize to the DNA sequence encoding the tobacco PMT root specific promoters disclosed herein will be at least 75%, 80%, 85%, 90% or even 95% homologous or more with the sequences of the DNA encoding the tobacco PMT root specific promoters disclosed herein.

Root specific promoters of the present invention are useful in directing tissue specific expression of transgenes in transformed plants. Such tissue-specific transgene expression is useful in providing resistance against damage caused by pests and pathogens which attack plant roots. In addition, as the root is a major sink organ for photosynthate storage, expression of transgenes designed to alter the stored carbohydrates may be directed by such promoters. Exogenous genes of particular interest for root specific expression include those that code for proteins that bind heavy metals (such as metallothionein); proteins that give resistance to soil borne pests and pathogens; proteins that confer resistance to heat, salt (salinity) and drought; proteins for desalinization; and proteins that metabolize plant storage compounds into alternative preferred products or forms.

The root specific promoters of the invention may be used to express proteins or peptides in "molecular farming" applications. Such proteins or peptides include but are not limited to industrial enzymes, antibodies, therapeutic agents, and nutritional products. Such root-specific expression is particularly useful when the plant is a root crop plant such as a sugar beet.

Root specific promoters of the invention are also useful for expressing an oligonucleotide that will decrease or inhibit expression of a native gene in the plant. Such oligonucleotides may be from 4, 6 or 8 nucleotides to 40, 80 or 100 nucleotides in length, or more, and may encode antisense oligonucleotides, ribozymes, sense suppression agents, or other products that inhibit the expression of a native gene.

Tissue specific promoters may also be used to convert pro-pesticides to active forms in selected tissue sites. Hsu et al. Pestic. Sci., 44, 9 (1995) report the use of a chimeric gene comprising the root-specific promoter TobRB7 and the B-glucuronidase enzyme gene, to preferentially convert a pro-pesticide to an active form in roots. The inactive pro-pesticide (a glucuronide of hydroxymethyloxamyl) was applied to foliage and was then transported through plant pbloem to roots, where it was converted to an active nematocidal form by glucuronidase.

Additionally, root-cortex specific promoters are useful for histological purposes, to identify or stain root-cortex tissue using a reporter gene such as B-glucurodinase.

The term "operatively associated," as used herein, refers to DNA sequences contained within a single DNA molecule which are associated so that the function of one is affected by the other. Thus, a promoter is operatively associated with a gene when it is capable of affecting the expression of that gene (i.e., the gene is under the transcriptional control of the promoter). The promoter is said to be "upstream" from the gene, which is in turn said to be "downstream" from the promoter.

DNA constructs, or "expression cassettes," of the present invention include, 5'–3' in the direction of transcription, a promoter of the present invention, a heterologous DNA segment operatively associated with the promoter, and, optionally, transcriptional and translational termination regions such as a termination signal and/or a polyadenylation region. These regulatory regions are preferably capable of operating in the transformed cells. The 3' termination region may be derived from the same gene as the transcriptional initiation region or from a different gene.

Plants may be divided into those lacking chlorophyll (such as fungi) and those containing chlorophyll (such as green algae, mosses); and further divided into those containing chlorophyll and having vascular tissue (such as ferns, gymnosperms, conifers, monocots and dicots). The latter group of plants includes those in which roots, stems and leaves may be present. As used herein, the term 'plant' encompasses all such organisms described above. As used herein, the 'term natural plant DNA' means DNA isolated from non-genetically altered, or untransformed, plants (for example, plant varieties which are produced by selective breeding).

As used herein, the term heterologous gene or heterologous DNA segment means a gene (or DNA segment) which is used to transform a cell by genetic engineering techniques, and which may not occur naturally in the cell. Structural genes are those portions of genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. Structural genes may encode a protein not normally found in the plant cell in which the gene is introduced or in combination with the promoter to which it is operationally associated. Genes which may be operationally associated with a promoter of the present invention for expression in a plant species may be derived from a chromosomal gene, cDNA, a synthetic gene, or combinations thereof. As used herein, the term heterologous DNA segment also includes DNA segments coding for non-protein products, such as ribozymes or anti-sense RNAs. Antisense RNAs are well known (see, e.g., U.S. Pat. No. 4,801,540 (Calgene, Inc.)).

Genes of interest for use with the present invention in plants include those affecting a wide variety of phenotypic and non-phenotypic properties. Among the phenotypic properties are proteins, such as enzymes, which provide resistance to various environmental stresses, including but not limited to stress caused by dehydration (resulting from heat, salinity or drought), herbicides, toxic metals, trace elements, pests and pathogens. Resistance may be due to a change in the target site, enhancement of the amount of a target protein in the host cell, increased amounts of one or more enzymes involved with the biosynthetic pathway of a product which protects the host against the stress, and the like. Structural genes may be obtained from prokaryotes or eukaryotes, bacteria, fungi, (e.g., from yeast, viruses, plants, and mammals) or may be synthesized in whole or in part. Illustrative genes include glyphosphate resistant 3-enolpyruvylphosphoshikinate synthase gene, nitrilase, genes in the proline and glutamine biosynthetic pathway, and metallothioneins.

Structural genes operatively associated with the promoter of the present invention may be those which code for a protein toxic to insects, such as a *Bacillus thuringiensis* crystal protein toxic to insects. A DNA sequence encoding a *B. thuringiensis* toxin toxic to Coleoptera, and variations of this sequence wherein the toxicity is retained, is disclosed in U.S. Pat. No. 4,853,331 (see also U.S. Pat. Nos. 4,918,006 and 4,910,136) (the disclosures of all U.S. Patent references cited herein are to be incorporated herein in their entirety by reference). A gene sequence from *B. thuringiensis* which renders plant species toxic to Lepidoptera is disclosed in PCT Application WO 90/02804. PCT Application WO 89/04868 discloses transgenic plants transformed with a vector which promotes the expression of a *B. thuringiensis* crystal protein, the sequence of which may be employed in connection with the present invention. PCT Application WO 90/06999 discloses DNA encoding a *B. thuringiensis* crystal protein toxin active against Lepidoptera. Another gene sequence encoding an insecticidal crystal protein is disclosed in U.S. Pat. No. 4,918,006. Exemplary of gene sequences encoding other insect toxins are gene sequences encoding a chitinase (e.g., EC-3.2.1.14), as disclosed in U.S. Pat. No. 4,940,840 and PCT Appln. No. WO 90/07001. A gene coding for a nematode-inducible pore protein useful in producing transgenic plants resistant to root nematodes is disclosed in U.S. patent application Ser. No. 08/007,998. Strains of *B. thuringiensis* which produce polypeptide toxins active against nematodes are disclosed in U.S. Pat. Nos. 4,948,734 and 5,093,120.

Where the expression product of the gene is to be located in a cellular compartment other than the cytoplasm, the structural gene may be constructed to include regions which code for particular amino acid sequences which result in translocation of the product to a particular site, such as the cell plasma membrane, or secretion into the periplasmic space or into the external environment of the cell. Various secretory leaders, membrane integration sequences, and translocation sequences for directing the peptide expression product to a particular site are described in the literature. See, for example, Cashmore et al., Biotechnology (1985) 3:803–808, Wickner and Lodish, Science (1985) 230:400–407.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there may be at least one marker present, which may be useful in one or more hosts, or different markers for individual hosts. That is, one marker may be employed for selection in a prokaryotic host while another marker may be employed for selection in a eukaryotic host, particularly the plant host. The markers may provide protection against a biocide, such as antibiotics, toxins, heavy metals, or the like; may provide complementation by imparting prototrophy to an auxotrophic host; or may provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase (GUS) (providing indigo production), luciferase (providing visible light production), NPTII (providing kanamycin resistance or G418 resistance), HPT (providing hygromycin resistance), and the mutated aroA gene (providing glyphosate resistance).

The various fragments comprising the various constructs, expression cassettes, markers, and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature. See, e.g., Maniatis et al., Molecular Cloning: A Laboratory Manual, Cold Spring Harbor Laboratory, Cold Spring Harbor, N.Y. (1982).

A vector is a replicable DNA construct. Vectors which may be used to transform plant tissue with DNA constructs of the present invention include both Agrobacterium vectors and ballistic vectors, as well as vectors suitable for DNA-mediated transformation. Agrobacterium tumefaciens cells containing a DNA construct of the present invention, wherein the DNA construct comprises a Ti plasmid, are useful in methods of making transformed plants. Plant cells are infected with an Agrobacterium tumefaciens to produce a transformed plant cell, and then a plant is regenerated from the transformed plant cell.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T-DNA region, and a second plasmid having a T-DNA region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0 270 356, titled "Pollen-mediated Plant Transformation". When using ballistic transformation procedures, the expression cassette may be incorporated into a plasmid capable of replicating in the cell to be transformed. Examples of microparticles suitable for use in such systems include 1 to 5 .mu.m gold spheres. The DNA construct may be deposited on the microparticle by any suitable technique, such as by precipitation.

A transformed host cell is a cell which has been transformed or transfected with constructs containing a DNA sequence as disclosed herein using recombinant DNA techniques. Plant species may be transformed with the DNA construct of the present invention by the DNA-mediated transformation of plant cell protoplasts and subsequent regeneration of the plant from the transformed protoplasts in accordance with procedures well known in the art.

The promoter sequences disclosed herein may be used to express a heterologous DNA sequence in any plant species capable of utilizing the promoter (i.e., any plant species the RNA polymerase of which binds to the promoter sequences disclosed herein). Examples of plant species suitable for transformation with the DNA constructs of the present invention include both monocots and dicots, and include but are not limited to tobacco, soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola. Thus an illustrative category of plants which may be transformed with the DNA constructs of the present invention are the dicots, and a more particular category of plants which may be transformed using the DNA constructs of the present invention are members of the family Solanacae.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

The examples which follow are provided to illustrate various specific embodiments of the present invention, and are not to be construed as limiting the invention.

EXAMPLE 1

Cloning of the NtPMT Promoter

Using the PMT cDNA sequence published by N. Hibi et al., *Plant Cell* 6, 723–725 (1994) we designed nested, divergent PCR primers for Inverse-PCR. Tobacco genomic DNA was cut with a variety of restriction endonucleases, ligated at low DNA concentrations (to promote circularization), and then used as a template for Inverse-PCR. The longest amplification product was obtained from genomic DNA that had been digested with NdeI. This fragment was cloned and sequenced. Sequence comparisons to the PMT cDNA showed sequence identity in the known regions, illustrating that the amplified DNA product was, indeed, the 5' flanking region of the PMT gene. The DNA sequence of the NtPMT promoter is as follows:

```
GTATACCAAA AATCAATTCA ACCCCCAAAA CATAATACAA

CCAATGTTAA TGCAATATCT CTGCTGCTAT CACGAAGATA

ATTGTAGCTC ACGAAAGTAG GATACATTAT GTAGGTTACA

TCACATAGAG GTAATCTAAA GCTCCCAATA ATAAGATGTG

TAATGTTGAT TATGTAGAAA TTTGCCAGGT TATTTAGAAT
```

-continued

```
AAACAAGAAG AGGAGAAAAA AAGTACAATT TACCTGAACT

CTTGAATGTA TCCTACAAAT AACCTAGACT TCATGGACGT

CAGTTGTCAG TTTACTTTTG TTTTAATGGT ACATCATTTG

TCAAATACTT TATTTGGATA AAAACAGTTT TGCCTAAGGA

GTAAACAGAT CCGGAGTAAG AAAGCAGACG ATTAAAGCAA

TTTTTAAAAA AGGAGAGAGA AATTAATGAG CACACACATA

TACTAGTGAA ATTAGGGTAC TAATTTACTA ATAATTGCAC

CGAGACAAAC TTATATTTTA GTTCCAAAAT GTCAGTCTAA

CCCTGCACGT TGTAATAAAT TTTTAACTCT ATTATATTAT

ATCGAGTTGC GCCCTCCACT CCTCGGTGTC CAAATTGTAT

TTAAATGCAT AGATGTTTAA TGGGAGTGTA CAGCAAGCTT

TCGGAAAATA CAAACCATAA TACTTTCTCT TCTTCAATTT

GTTTAGTTTA ATTTTGAAAA TGGAAGTCAT ATCTACCAAC

ACAAATGGCT CTACCATCTT CA
```

The sequence corresponding to the PMT cDNA published by Hibi et al. supra, is underlined. The initiating ATG is in bold. The sequence used as a primer for inverse-PCR is in italics.

EXAMPLE 2

Transgenic Plants

The NtPMTI promoter set forth in Example 1 (SEQ ID NO: 1) was fused to the GUS gene in pBI101 and transformed into tobacco in accordance with standard techniques. See, e.g., U.S. Pat. No. 5,837,876 at Examples 4–6. Transgenic tobacco was stained for GUS activity using X-Gluc. Transgenic roots stained for GUS activity.

EXAMPLE 3

Deletion Mutants

Additional examples of PMT promoters of the present invention include deletion mutants of the promoter set forth in SEQ ID NO: 1 above. These include mutants with 5' regions deleted, as set forth in SEQ ID NO: 2–6 below, as follows:

```
AATCAATTCA ACCCCCAAAA CATAATACAA CCAATGTTAA    SEQ ID NO: 2

TGCAATATCT CTGCTGCTAT CACGAAGATA ATTGTAGCTC ACGAAAGTAG

GATACATTAT GTAGGTTACA TCACATAGAG GTAATCTAAA GCTCCCAATA

ATAAGATGTG TAATGTTGAT TATGTAGAAA TTTGCCAGGT TATTTAGAAT

AAACAAGAAG AGGAGAAAAA AAGTACAATT TACCTGAACT CTTGAATGTA

TCCTACAAAT AACCTAGACT TCATGGACGT CAGTTGTCAG TTTACTTTTG
```

-continued

```
TTTTAATGGT ACATCATTTG TCAAATACTT TATTTGGATA AAAACAGTTT

TGCCTAAGGA GTAAACAGAT CCGGAGTAAG AAAGCAGACG ATTAAAGCPA

TTTTTAAAAA AGGAGAGAGA AATTAATGAG CACACACATA TACTAGTGAA

ATTAGGGTAC TAATTTACTA ATAATTGCAC CGAGACAAAC TTATATTTTA

GTTCCAAAAT GTCAGTCTAA CCCTGCACGT TGTAATAAAT TTTTAACTCT

ATTATATTAT ATCGAGTTGC GCCCTCCACT CCTCGGTGTC CAAATTGTAT

TTAAATGCAT AGATGTTTAA TGGGAGTGTA CAGCAAGCTT TCGGAAAATA

CAAACCATAA TACTTTCTCT TCTTCAATTT GTTTAGTTTA ATTTTGAAAA

TGGAAGTCAT ATCTACCAAC ACAAATGGCT CTACCATCTT CA

ACCCCCAAAA CATAATACAA CCAATGTTAA    SEQ ID NO: 3

TGCAATATCT CTGCTGCTAT CACGAAGATA ATTGTAGCTC ACGAAAGTAG

GATACATTAT GTAGGTTACA TCACATAGAG GTAATCTAAA GCTCCCAATA

ATAAGATGTG TAATGTTGAT TATGTAGAAA TTTGCCAGGT TATTTAGAAT

AAACAAGAAG AGGAGAAAAA AAGTACAATT TACCTGAACT CTTGAATGTA

TCCTACAAAT AACCTAGACT TCATGGACGT CAGTTGTCAG TTTACTTTTG

TTTTAATGGT ACATCATTTG TCAAATACTT TATTTGGATA AAAACAGTTT

TGCCTAAGGA GTAAACAGAT CCGGAGTAAG AAAGCAGACG ATTAAAGCAA

TTTTTAAAAA AGGAGAGAGA AATTAATGAG CACACACATA TACTAGTGAA

ATTAGGGTAC TAATTTACTA ATAATTGCAC CGAGACAAAC TTATATTTTA

GTTCCAAAAT GTCAGTCTAA CCCTGCACGT TGTAATAAAT TTTTAACTCT

ATTATATTAT ATCGAGTTGC GCCCTCCACT CCTCGGTGTC CAAATTGTAT

TTAAATGCAT AGATGTTTAA TGGGAGTGTA CAGCAAGCTT TCGGAAAATA

CAAACCATAA TACTTTCTCT TCTTCAATTT GTTTAGTTTA ATTTTGAAAA

TGGAAGTCAT ATCTACCAAC ACAAATCGCT CTACCATCTT CA

CATAATACAA CCAATGTTAA SEQ ID NO: 4

TGCAATATCT CTGCTGCTAT CACGAAGATA ATTGTAGCTC ACGAAAGTAG

GATACATTAT GTAGGTTACA TCACATAGAG GTAATCTAAA GCTCCCAATA

ATAAGATGTG TAATGTTGAT TATGTAGAAA TTTGCCAGGT TATTTAGAAT

AAACAAGAAG AGGAGAAAAA AAGTACAATT TACCTGAACT CTTGAATGTA

TCCTACAAAT AACCTAGACT TCATGGACGT CAGTTGTCAG TTTACTTTTG

TTTTAATGGT ACATCATTTG TCAAATACTT TATTTGGATA AAAACAGTTT

TGCCTAAGGA GTAAACAGAT CCGGAGTAAG AAAGCAGACG ATTAAAGCAA

TTTTTAAAAA AGGAGAGAGA AATTAATGAG CACACACATA TACTAGTGAA

ATTAGGGTAC TAATTTACTA ATAATTGCAC CGAGACAAAC TTATATTTTA

GTTCCAAAAT GTCAGTCTAA CCCTGCACGT TGTAATAAAT TTTTAACTCT

ATTATATTAT ATCGAGTTGC GCCCTCCACT CCTCGGTGTC CAAATTGTAT
```

-continued

```
TTAAATGCAT AGATGTTTAA TGGGAGTGTA CAGCAAGCTT TCGGAAAATA

CAAACCATAA TACTTTCTCT TCTTCAATTT GTTTAGTTTA ATTTTGAAAA

TGGAAGTCAT ATCTACCAAC ACAAATGGCT CTACCATCTT CA

CCAATGTTAA SEQ ID NO: 5

TGCAATATCT CTGCTGCTAT CACGAAGATA ATTGTAGCTC ACGAAAGTAG

GATACATTAT GTAGGTTACA TCACATAGAG GTAATCTAAA GCTCCCAATA

ATAAGATGTG TAATGTTGAT TATGTAGAAA TTTGCCAGGT TATTTAGAAT

AAACAAGAAG AGGAGAAAAA AAGTACAATT TACCTGAACT CTTGAATGTA

TCCTACAAAT AACCTAGACT TCATGGACGT CAGTTGTCAG TTTACTTTTG

TTTTAATGGT ACATCATTTG TCAAATACTT TATTTGGATA AAAACAGTTT

TGCCTAAGGA GTAAACAGAT CCGGAGTAAG AAAGCAGACG ATTAAAGCAA

TTTTTAAAAA AGGAGAGAGA AATTAATGAG CACACACATA TACTAGTGAA

ATTAGGGTAC TAATTTACTA ATAATTGCAC CGAGACAAAC TTATATTTTA

GTTCCAAAAT GTCAGTCTAA CCCTGCACGT TGTAATAAAT TTTTAACTCT

ATTATATTAT ATCGAGTTGC GCCCTCCACT CCTCGGTGTC CAAATTGTAT

TTAAATGCAT AGATGTTTAA TGGGAGTGTA CAGCAAGCTT TCGGAAAATA

CAAACCATAA TACTTTCTCT TCTTCAATTT GTTTAGTTTA ATTTTGAAAA

TGGAAGTCAT ATCTACCAAC ACAAATCGCT CTACCATCTT CA

TGCAATATCT CTGCTGCTAT CACGAAGATA ATTGTAGCTC ACGAAAGTAG SEQ ID NO: 6

GATACATTAT GTAGGTTACA TCACATAGAG GTAATCTAAA GCTCCCAATA

ATAAGATGTG TAATGTTGAT TATGTAGAAA TTTGCCAGGT TATTTAGAAT

AAACAAGAAG AGGAGAAAAA AAGTACAATT TACCTGAACT CTTGAATGTA

TCCTACAAAT AACCTAGACT TCATGGACGT CAGTTGTCAG TTTACTTTTG

TTTTAATGGT ACATCATTTG TCAAATACTT TATTTGGATA AAAACAGTTT

TGCCTAAGGA GTAAACAGAT CCGGAGTAAG AAAGCAGACG ATTAAAGCAA

TTTTTAAAAA AGGAGAGAGA AATTAATGAG CACACACATA TACTAGTGAA

ATTAGGGTAC TAATTTACTA ATAATTGCAC CGAGACAAAC TTATATTTTA

GTTCCAAAAT GTCAGTCTAA CCCTGCACGT TGTAATAAAT TTTTAACTCT

ATTATATTAT ATCGAGTTGC GCCCTCCACT CCTCGGTGTC CAAATTGTAT

TTAAATGCAT AGATGTTTAA TGGGAGTGTA CAGCAAGCTT TCGGAAAATA

CAAACCATAA TACTTTCTCT TCTTCAATTT GTTTAGTTTA ATTTTGAAAA

TGGAAGTCAT ATCTACCAAC ACAAATGGCT CTACCATCTT CA
```

Additional examples of PMT promoters of the present invention include deletion mutants of the sequence given as SEQ ID NO: 1 above, in which 3' regions are deleted. Examples include SEQ ID NO: 7–9 below:

```
GTATACCAAA AATCAATTCA ACCCCCAAAA CATAATACAA CCAATGTTAA SEQ ID NO: 7

TGCAATATCT CTGCTGCTAT CACGAAGATA ATTGTAGCTC ACGAAAGTAG
```

-continued
```
GATACATTAT GTAGGTTACA TCACATAGAG GTAATCTAAA GCTCCCAATA
ATAAGATGTG TAATGTTGAT TATGTAGAAA TTTGCCAGGT TATTTAGAAT
AAACAAGAAG AGGAGAAAAA AAGTACAATT TACCTGAACT CTTGAATGTA
TCCTACAAAT AACCTAGACT TCATGGACGT CAGTTGTCAG TTTACTTTTG
TTTTAATGGT ACATCATTTG TCAAATACTT TATTTGGATA AAAACAGTTT
TGCCTAAGGA GTAAACAGAT CCGGAGTAAG AAAGCAGACG ATTAAAGCAA
TTTTTAAAAA AGGAGAGAGA AATTAATGAG CACACACATA TACTAGTGAA
ATTAGGGTAC TAATTTACTA ATAATTGCAC CGAGACAAAC TTATATTTTA
GTTCCAAAAT GTCAGTCTAA CCCTGCACGT TGTAATAAAT TTTTAACTCT
ATTATATTAT ATCGAGTTGC GCCCTCCACT CCTCGGTGTC CAAATTGTAT
TTAAATGCAT AGATGTTTAA TGGGAGTGTA CAGCAAGCTT TC GTATACCAAA AATCAATTCA ACCCCCAAAA CATAATACAA CCAATGTTAA    SEQ ID NO: 8
TGCAATATCT CTGCTGCTAT CACGAAGATA ATTGTAGCTC ACGAAAGTAG
GATACATTAT GTAGGTTACA TCACATAGAG GTAATCTAAA GCTCCCAATA
ATAAGATGTG TAATGTTGAT TATGTAGAAA TTTGCCAGGT TATTTAGAAT
AAACAAGAAG AGGAGAAAAA AAGTACAATT TACCTGAACT CTTGAATGTA
TCCTACAAAT AACCTAGACT TCATGGACGT CAGTTGTCAG TTTACTTTTG
TTTTAATGGT ACATCATTTG TCAAATACTT TATTTGGATA AAAACAGTTT
TGCCTAAGGA GTAAACAGAT CCGGAGTAAG AAAGCAGACG ATTAAAGCAA
TTTTTAAAAA AGGAGAGAGA AATTAATGAG CACACACATA TACTAGTGAA
ATTAGGGTAC TAATTTACTA ATAATTGCAC CGAGACAAAC TTATATTTTA
GTTCCAAAAT GTCAGTCTAA CCCTGCACGT TGTAATAAAT TTTTAACTCT
ATTATATTAT ATCGAGTTGC GCCCTCCACT CCTCGGTGTC CAAATTGTAT
TTAAATGCAT AGATGTTTAA TGGGAGTGTA GTATACCAAA AATCAATTCA ACCCCCAAAA CATAATACAA CCAATGTTAA    SEQ ID NO: 9
TGCAATATCT CTGCTGCTAT CACGAAGATA ATTGTAGCTC ACGAAAGTAG
GATACATTAT GTAGGTTACA TCACATAGAG GTAATCTAAA GCTCCCAATA
ATAAGATGTG TAATGTTGAT TATGTAGAAA TTTGCCAGGT TATTTAGAAT
AAACAAGAAG AGGAGAAAAA AAGTACAATT TACCTGAACT CTTGAATGTA
TCCTACAAAT AACCTAGACT TCATGGACGT CAGTTGTCAG TTTACTTTTG
TTTTAATGGT ACATCATTTG TCAAATACTT TATTTGGATA AAAACAGTTT
TGCCTAAGGA GTAAACAGAT CCGGAGTAAG AAAGCAGACG ATTAAAGCAA
TTTTTAAAAA AGGAGAGAGA AATTAATGAG CACACACATA TACTAGTGAA
ATTAGGGTAC TAATTTACTA ATAATTGCAC CGAGACAAAC TTATATTTTA
GTTCCAAAAT GTCAGTCTAA CCCTGCACGT TGTAATAAAT TTTTAACTCT
ATTATATTAT ATCGAGTTGC GCCCTCCACT CCTCGGTGTC CAAATTGTAT
TTAAATGCAT AGATGTTTAA
```

Still additional examples of PMT promoters of the present invention include deletion mutants of the sequence given as SEQ ID NO: 1 above, in which both 3' and 5' regions are deleted. Examples include SEQ ID NO: 10–11 below:

```
          AATCAATTCA ACCCCCAAAA CATAATACAA CCAATGTTAA SEQ ID NO: 10
TGCAATATCT CTGCTGCTAT CACGAAGATA ATTGTAGCTC ACGAAAGTAG
GATACATTAT GTAGGTTACA TCACATAGAG GTAATCTAAA GCTCCCAATA
ATAAGATGTG TAATGTTGAT TATGTAGAAA TTTGCCAGGT TATTTAGAAT
AAACAAGAAG AGGAGAAAAA AAGTACAATT TACCTGAACT CTTGAATGTA
TCCTACAAAT AACCTAGACT TCATGGACGT CAGTTGTCAG TTTACTTTTG
TTTTAATGGT ACATCATTTG TCAAATACTT TATTTGGATA AAAACAGTTT
TGCCTAAGGA GTAAACAGAT CCGGAGTAAG AAAGCAGACG ATTAAAGCAA
TTTTTAAAAA AGGAGAGAGA AATTAATGAG CACACACATA TACTAGTGAA
ATTAGGGTAC TAATTTACTA ATAATTGCAC CGAGACAAAC TTATATTTTA
GTTCCAAAAT GTCAGTCTAA CCCTGCACGT TGTAATAAAT TTTTAACTCT
ATTATATTAT ATCGAGTTGC GCCCTCCACT CCTCGGTGTC CAAATTGTAT
TTAAATGCAT AGATGTTTAA TGGGAGTGTA CAGCAAGCTT
```

```
                     ACCCCCAAAA CATAATACAA CCAATGTTAA SEQ ID NO: 11
TGCAATATCT CTGCTGCTAT CACGAAGATA ATTGTAGCTC ACGAAAGTAG
GATACATTAT GTAGGTTACA TCACATAGAG GTAATCTAAA GCTCCCAATA
ATAAGATGTG TAATGTTGAT TATGTAGAAA TTTGCCAGGT TATTTAGAAT
AAACAAGAAG AGGAGAAAAA AAGTACAATT TACCTGAACT CTTGAATGTA
TCCTACAAAT AACCTAGACT TCATGGACGT CAGTTGTCAG TTTACTTTTG
TTTTAATGGT ACATCATTTG TCAAATACTT TATTTGGATA AAAACAGTTT
TGCCTAAGGA GTAAACAGAT CCGGAGTAAG AAAGCAGACG ATTAAAGCAA
TTTTTAAAAA AGGAGAGAGA AATTAATGAG CACACACATA TACTAGTGAA
ATTAGGGTAC TAATTTACTA ATAATTGCAC CGAGACAAAC TTATATTTTA
GTTCCAAAAT GTCAGTCTAA CCCTGCACGT TGTAATAAAT TTTTAACTCT
ATTATATTAT ATCGAGTTGC GCCCTCCACT CCTCGGTGTC CAAATTGTAT
TTAAATGCAT AGATGTTTAA TGGGAGTGTA:
```

All of the foregoing SEQ ID Nos: 2–11 may be operatively associated with a heterologous nucleic acid or DNA of interest as described above to produce a recombinant nucleic acid which can be inserted into a vector, and in turn into a plant cell and transgenic plants as described above, to cause expression of the heterologous nucleic acid or DNA in the plant.

EXAMPLE 4

Expression Analysis

FIG. 1 shows average GUS expression levels in leaves (column 1), stems (column 2), and roots (column 3) directed by the PMT promoter. Data for all 48 independent transformants we examined. There was substantial variation among the GUS levels from transformant to tmnsformant. Important to note is the average GUS activity level (pmol MU/mg protein/min) for roots is 544.82, for stems is 13.24 (~40-fold enhancement in roots), and for leaves is 0.26 (~2000-fold enhancement in roots). Also note that the majority of leaves (44/48) and stems (40/48) had no GUS activity.

The foregoing is illustrative of the present invention, and is not to be construed as limiting thereof. The invention is defined by the following claims, with equivalents of the claims to be included therein.

That which is claimed is:

1. An isolated DNA molecule which directs root specific transcription in a plant cell, said isolated DNA molecule comprising a nucleotide sequence selected from the group consisting of: of SEQ ID NO:1, SEQ ID NO:2, SEQ ID NO:3, SEQ ID NO:4, SEQ ID NQ:5, SEQ ID NO:6, SEQ ID NO:7, SEQ ID NO:8, SEQ ID NO:9, SEQ ID NO: 10 and SEQ ID NO:11.

2. The DNA molecule of claim 1, comprising the nucleotide sequence of SEQ ID NO:10.

3. The DNA molecule of claim 1, comprising the nucleotide sequence of SEQ ID NO:9.

4. The DNA molecule of claim 1, comprising the nucleotide sequence of SEQ ID NO:8.

5. The DNA molecule of claim 1, comprising the nucleotide sequence of SEQ ID NO:7.

6. The DNA molecule of claim 1, comprising the nucleotide sequence of SEQ ID NO:6.

7. The DNA molecule of claim 1, comprising the nucleotide sequence of SEQ ID NO:5.

8. The DNA molecule of claim 1, comprising the nucleotide sequence of SEQ ID NO:4.

9. The DNA molecule of claim 1, comprising the nucleotide sequence of SEQ ID NO:3.

10. The DNA molecule of claim 1, comprising the nucleotide sequence of SEQ ID NO:2.

11. The DNA molecule of claim 1, comprising the nucleotide sequence of SEQ ID NO:1.

12. The DNA molecule of claim 1, comprising the nucleotide sequence of SEQ ID NO:11.

13. A DNA construct comprising, in the 5' to 3' direction, a root specific promoter and a heterologous DNA sequence downstream from said promoter and operatively associated therewith, wherein said root specific promoter comprises a nucleotide sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, and SEQ ID NO: 11.

14. The DNA construct according to claim 13, wherein said construct is a plasmid.

15. The DNA construct according to claim 13, wherein said heterologous DNA sequence is a gene coding for an insecticidal protein.

16. The DNA construct according to claim 14, wherein said heterologous DNA sequence is a gene coding for a *Bacillus thuringiensis* crystal protein toxic to insects.

17. A plant cell transformed with the DNA construct according to claim 13.

18. A method of making a transformed plant, comprising regenerating a plant from the plant cell according to claim 17.

19. A cell containing the DNA construct according to claim 13, and wherein said DNA construct further comprises a Ti plasmid.

20. A method of making a transformed plant, comprising infecting a plant cell with the construct according to claim 19 to produce a transformed plant cell, and then regenerating a plant from said transformed plant cell.

21. A microparticle carrying the DNA construct according to claim 13, wherein said microparticle is suitable for the ballistic transformation of a plant cell.

22. A method of making a transformed plant, comprising propelling the microparticle according to claim 21 into a plant cell to produce a transformed plant cell, and then regenerating a plant from said transformed plant cell.

23. A plant cell protoplast comprising the DNA construct according to claim 13.

24. A method of making a transformed plant, comprising regenerating a plant from the plant cell protoplast according to claim 23.

25. A transformed plant comprising transformed plant cells, said transformed plant cells comprising a heterologous DNA construct, which construct comprises in the 5' to 3' direction, a root specific promoter and a heterologous DNA sequence downstream from said promoter and operatively associated therewith, said promoter directing root specific transcription of said heterologous DNA sequence and wherein said promoter comprises a nucleotide sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO: 11.

26. The transformed plant according to claim 25, wherein said plant is a dicot.

27. The transformed plant according to claim 25, wherein said plant is a monocot.

28. The transformed plant according to claim 25, wherein said plant is a tobacco plant.

29. An isolated DNA molecule consisting essentially of a promoter which directs root specific transcription in a plant cell and, wherein said promoter comprises a nucleotide sequence selected from the group consisting of SEQ ID NOs:1–11.

30. A DNA construct comprising an expression cassette, wherein said construct comprises, in the 5' to 3' direction, the DNA molecule according to claim 29 and a heterologous DNA sequence downstream from said promoter and operatively associated therewith.

31. A transformed plant comprising transformed plant cells, said transformed plant cells containing the DNA construct according to claim 30.

* * * * *

UNITED STATES PATENT AND TRADEMARK OFFICE
CERTIFICATE OF CORRECTION

| | | |
|---|---|---|
| PATENT NO. | : 7,189,570 B2 | Page 1 of 1 |
| APPLICATION NO. | : 10/416120 | |
| DATED | : March 13, 2007 | |
| INVENTOR(S) | : Conkling et al. | |

It is certified that error appears in the above-identified patent and that said Letters Patent is hereby corrected as shown below:

Column 10, Line 36: Please correct "NtPMTI" To read --NtPMT1--

Column 27, Line 39: Please correct "SEQ ID NQ:5," To read --SEQ ID NO:5,--

Signed and Sealed this

Twenty-sixth Day of June, 2007

JON W. DUDAS
*Director of the United States Patent and Trademark Office*